(12) United States Patent
Malofsky et al.

(10) Patent No.: US 10,414,839 B2
(45) Date of Patent: Sep. 17, 2019

(54) POLYMERS INCLUDING A METHYLENE BETA-KETOESTER AND PRODUCTS FORMED THEREFROM

(71) Applicant: SIRRUS, INC., Loveland, OH (US)

(72) Inventors: Bernard M. Malofsky, Bloomfield, CT (US); Adam G. Malofsky, Loveland, OH (US); Tanmoy Dey, Willington, CT (US); Jeffrey M. Sullivan, Goshen, OH (US)

(73) Assignee: Sirrus, Inc., Loveland, OH (US)

( * ) Notice: Subject to any disclaimer, the term of this patent is extended or adjusted under 35 U.S.C. 154(b) by 0 days.

(21) Appl. No.: 15/661,893

(22) Filed: Jul. 27, 2017

(65) Prior Publication Data

US 2017/0355789 A1 Dec. 14, 2017

Related U.S. Application Data

(60) Continuation-in-part of application No. 15/363,169, filed on Nov. 29, 2016, and a continuation-in-part of
(Continued)

(51) Int. Cl.
| | |
|---|---|
| *C08F 20/28* | (2006.01) |
| *C08F 20/38* | (2006.01) |
| *C08F 22/20* | (2006.01) |
| *C08K 5/00* | (2006.01) |
| *C08L 21/00* | (2006.01) |
| *C08L 33/14* | (2006.01) |
| *C08L 33/16* | (2006.01) |
| *C08L 35/02* | (2006.01) |
| *C09J 133/14* | (2006.01) |
| *C07D 307/54* | (2006.01) |
| *C09D 133/14* | (2006.01) |
| *C09D 133/16* | (2006.01) |
| *C09D 135/02* | (2006.01) |

(Continued)

(52) U.S. Cl.
CPC ............. *C08F 20/28* (2013.01); *C07C 45/75* (2013.01); *C07C 49/794* (2013.01); *C07C 49/796* (2013.01); *C07C 49/798* (2013.01); *C07C 49/80* (2013.01); *C07C 67/03* (2013.01); *C07C 67/30* (2013.01); *C07C 67/333* (2013.01); *C07C 67/343* (2013.01); *C07C 69/604* (2013.01); *C07C 69/738* (2013.01); *C07D 307/46* (2013.01); *C07D 307/54* (2013.01); *C07D 333/22* (2013.01); *C07D 333/24* (2013.01); *C08F 20/14* (2013.01); *C08F 20/30* (2013.01); *C08F 20/38* (2013.01); *C08F 20/68* (2013.01); *C08F 22/20* (2013.01); *C08F 24/00* (2013.01); *C08F 28/06* (2013.01); *C08F 116/36* (2013.01); *C08F 128/06* (2013.01); *C08F 222/14* (2013.01); *C08K 3/013* (2018.01); *C08K 5/0008* (2013.01); *C08L 21/00* (2013.01); *C08L 33/14* (2013.01); *C08L 33/16* (2013.01); *C08L 35/02* (2013.01); *C09D 4/00* (2013.01); *C09D 129/12* (2013.01); *C09D 133/14* (2013.01); *C09D 133/16* (2013.01); *C09D 135/02* (2013.01); *C09D 141/00* (2013.01); *C09J 4/00* (2013.01); *C09J 133/06* (2013.01); *C09J 133/14* (2013.01); *C09J 133/16* (2013.01); *C09J 135/02* (2013.01); *C07C 2601/02* (2017.05); *C07C 2601/04* (2017.05); *C07C 2601/08* (2017.05); *C07C 2601/14* (2017.05); *C08F 222/1006* (2013.01); *C08K 5/005* (2013.01); *C08K 5/08* (2013.01); *C08K 5/13* (2013.01); *Y02P 20/127* (2015.11)

(58) Field of Classification Search
None
See application file for complete search history.

(56) References Cited

U.S. PATENT DOCUMENTS

| | | |
|---|---|---|
| 2,212,506 A | 8/1940 | Bachman |
| 2,245,567 A | 6/1941 | Brant et al. |
| | (Continued) | |

FOREIGN PATENT DOCUMENTS

| | | |
|---|---|---|
| CN | 102901754 A | 1/2013 |
| DE | 19508049 A1 | 9/1996 |
| | (Continued) | |

OTHER PUBLICATIONS

Fioravanti et al. "Functionalized enomes as starting materials for the construction of aziridine scaffolds", Molecular Diversity, 2003, 6:3-4, 177-180 (Year: 2003).*

(Continued)

*Primary Examiner* — Nicole M. Buie-Hatcher
(74) *Attorney, Agent, or Firm* — Young Basile Hanlon & MacFarlane, P.C.

(57) ABSTRACT

The present teachings are directed at 1,1-disubstituted alkene monomers (e.g., methylene beta-ketoester monomers), methods for producing the same, polymerizable compositions including a methylene beta-ketoester monomer, and polymers, compositions and products formed therefrom. The monomer preferably is a high purity monomer. In the method for producing the methylene beta-ketoesters of the invention, a beta-ketoester may be reacted with a source of formaldehyde. The methylene beta-ketoester monomers may be used in monomer-based products (e.g., inks, adhesives, coatings, sealants or reactive molding) and polymer-based products (e.g., fibers, films, sheets, medical polymers, composite polymers and surfactants).

7 Claims, 9 Drawing Sheets

Related U.S. Application Data application No. 14/868,795, filed on Sep. 29, 2015, now Pat. No. 9,828,324, which is a continuation-in-part of application No. 14/810,741, filed on Jul. 28, 2015, now Pat. No. 9,279,022, which is a continuation-in-part of application No. 14/789,178, filed on Jul. 1, 2015, now Pat. No. 9,249,265, and a continuation-in-part of application No. 14/352,369, filed on Apr. 17, 2014, now Pat. No. 9,221,739, which is a division of application No. 14/352,406, filed on Apr. 17, 2014, now Pat. No. 9,527,795, and a continuation-in-part of application No. 14/075,334, filed on Nov. 8, 2013, which is a continuation of application No. 13/880,438, filed as application No. PCT/US2012/060840, filed as application No. PCT/US2012/060837, filed as application No. PCT/US2011/056903 on Oct. 19, 2011, now Pat. No. 8,609,885.

(60) Provisional application No. 62/186,479, filed on Jun. 30, 2015, provisional application No. 62/182,076, filed on Jun. 19, 2015, provisional application No. 62/047,283, filed on Sep. 8, 2014, provisional application No. 62/047,328, filed on Sep. 8, 2014, provisional application No. 61/549,152, filed on Oct. 19, 2011, provisional application No. 61/549,092, filed on Oct. 19, 2011, provisional application No. 61/549,104, filed on Oct. 19, 2011, provisional application No. 61/523,705, filed on Aug. 15, 2011, provisional application No. 61/523,311, filed on Aug. 13, 2011, provisional application No. 61/405,049, filed on Oct. 20, 2010, provisional application No. 61/405,029, filed on Oct. 20, 2010, provisional application No. 61/405,056, filed on Oct. 20, 2010, provisional application No. 61/405,078, filed on Oct. 20, 2010, provisional application No. 61/405,033, filed on Oct. 20, 2010.

(51) Int. Cl.

| | | |
|---|---|---|
| C09J 135/02 | (2006.01) | |
| C09J 133/16 | (2006.01) | |
| C07C 49/80 | (2006.01) | |
| C07C 69/604 | (2006.01) | |
| C07C 67/03 | (2006.01) | |
| C09J 133/06 | (2006.01) | |
| C07D 307/46 | (2006.01) | |
| C07C 49/794 | (2006.01) | |
| C07C 49/796 | (2006.01) | |
| C07C 49/798 | (2006.01) | |
| C09D 141/00 | (2006.01) | |
| C07D 333/22 | (2006.01) | |
| C08F 116/36 | (2006.01) | |
| C08F 128/06 | (2006.01) | |
| C09D 129/12 | (2006.01) | |
| C07C 45/75 | (2006.01) | |
| C07D 333/24 | (2006.01) | |
| C08F 20/68 | (2006.01) | |
| C08F 24/00 | (2006.01) | |
| C07C 67/30 | (2006.01) | |
| C08F 222/14 | (2006.01) | |
| C08F 28/06 | (2006.01) | |
| C07C 69/738 | (2006.01) | |
| C08F 20/30 | (2006.01) | |
| C08K 3/013 | (2018.01) | |
| C07C 67/333 | (2006.01) | |
| C07C 67/343 | (2006.01) | |
| C08F 20/14 | (2006.01) | |
| C09D 4/00 | (2006.01) | |
| C09J 4/00 | (2006.01) | |
| C08F 222/10 | (2006.01) | |
| C08K 5/08 | (2006.01) | |
| C08K 5/13 | (2006.01) | |

(56) References Cited

U.S. PATENT DOCUMENTS

| | | | |
|---|---|---|---|
| 2,403,791 | A | 7/1941 | D'Aiello |
| 2,277,479 | A | 3/1942 | D'Aiello |
| 2,313,501 | A | 3/1943 | Bachman et al. |
| 2,330,033 | A | 9/1943 | D'Aiello |
| 2,569,797 | A | 9/1948 | Campbell |
| 2,569,767 | A | 10/1951 | Knock |
| 2,730,457 | A | 1/1956 | Green et al. |
| 3,042,710 | A | 7/1962 | Dickstein et al. |
| 3,197,318 | A | 7/1965 | Halpern et al. |
| 3,203,915 | A | 8/1965 | D'Aiello |
| 3,221,745 | A | 12/1965 | Coover et al. |
| 3,427,250 | A | 2/1969 | Haas et al. |
| 3,489,663 | A | 1/1970 | Bayer et al. |
| 3,523,097 | A | 8/1970 | Coover et al. |
| 3,557,185 | A | 1/1971 | Ito et al. |
| 3,591,676 | A | 7/1971 | Hawkins |
| 3,595,869 | A | 7/1971 | Shuman |
| 3,677,989 | A | 7/1972 | Jenkinson |
| 3,758,550 | A | 9/1973 | Eck et al. |
| 3,923,836 | A | 12/1975 | Bender |
| 3,936,486 | A | 2/1976 | Egger et al. |
| 3,940,362 | A | 2/1976 | Overhurlts |
| 3,945,891 | A | 3/1976 | Aal et al. |
| 3,966,562 | A | 6/1976 | Mukushi et al. |
| 3,975,422 | A | 8/1976 | Buck |
| 3,978,422 | A | 8/1976 | Rheinfelder |
| 3,995,489 | A | 12/1976 | Smith et al. |
| 4,001,345 | A | 1/1977 | Gorton et al. |
| 4,004,984 | A | 1/1977 | Margen |
| 4,018,656 | A | 4/1977 | Rogers et al. |
| 4,035,243 | A | 7/1977 | Katz et al. |
| 4,036,985 | A | 7/1977 | Amato et al. |
| 4,046,943 | A | 9/1977 | Smith et al. |
| 4,049,698 | A | 9/1977 | Hawkins et al. |
| 4,056,543 | A | 11/1977 | Ponticello |
| 4,079,058 | A | 3/1978 | Ackermann et al. |
| 4,080,238 | A | 3/1978 | Wolinski et al. |
| 4,083,751 | A | 4/1978 | Choi et al. |
| 4,102,809 | A | 7/1978 | Smith et al. |
| 4,105,688 | A | 8/1978 | Arni et al. |
| 4,118,422 | A | 10/1978 | Klein |
| 4,140,584 | A | 2/1979 | Margen |
| 4,148,693 | A | 4/1979 | Williamson |
| 4,154,914 | A | 5/1979 | Kuraya |
| 4,160,864 | A | 7/1979 | Ponticello et al. |
| 4,176,012 | A | 11/1979 | Bryant |
| 4,186,058 | A | 1/1980 | Katz et al. |
| 4,186,060 | A | 1/1980 | Katz et al. |
| 4,198,334 | A | 4/1980 | Rasberger |
| 4,224,112 | A | 9/1980 | Childs |
| 4,229,263 | A | 10/1980 | Childs |
| 4,236,975 | A | 12/1980 | Childs |
| 4,237,297 | A | 12/1980 | Rody et al. |
| 4,243,493 | A | 1/1981 | Gruber et al. |
| 4,256,908 | A | 3/1981 | Nishimura et al. |
| 4,282,067 | A | 8/1981 | Katz et al. |
| 4,282,071 | A | 8/1981 | Sherrod |
| 4,291,171 | A | 9/1981 | Baum et al. |
| 4,313,865 | A | 2/1982 | Teramoto et al. |
| 4,319,964 | A | 3/1982 | Katz et al. |
| 4,329,479 | A | 5/1982 | Yabutani et al. |
| 4,396,039 | A | 8/1983 | Klenk et al. |
| 4,399,300 | A | 8/1983 | Prange et al. |
| 4,411,740 | A | 10/1983 | Flanigam et al. |
| 4,440,601 | A | 4/1984 | Katz et al. |
| 4,440,910 | A | 4/1984 | O'Connor |
| 4,443,624 | A | 4/1984 | Prange et al. |

(56) References Cited

U.S. PATENT DOCUMENTS

| | | |
|---|---|---|
| 4,444,928 A | 4/1984 | Karrer |
| 4,450,067 A | 5/1984 | Angevine et al. |
| 4,503,074 A | 3/1985 | Friedman |
| 4,504,658 A | 3/1985 | Narisada et al. |
| 4,510,273 A | 4/1985 | Miura et al. |
| 4,517,105 A | 5/1985 | Laemmle et al. |
| 4,523,007 A | 6/1985 | Schipfer et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,724,053 A | 2/1988 | Jasne |
| 4,727,701 A | 3/1988 | Figari |
| 4,728,701 A | 3/1988 | Jarvis et al. |
| 4,736,056 A | 4/1988 | Smith et al. |
| 4,743,106 A | 5/1988 | Novicky |
| 4,767,503 A | 8/1988 | Crescentini et al. |
| 4,769,464 A | 9/1988 | Sajtos |
| 4,783,242 A | 11/1988 | Robbins |
| 4,828,882 A | 5/1989 | Tsezos et al. |
| 4,835,153 A | 5/1989 | Kabota et al. |
| 4,840,949 A | 6/1989 | Korbonits et al. |
| 4,897,473 A | 1/1990 | Dombek |
| 4,914,226 A | 4/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,397,812 A | 3/1995 | Usami et al. |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 10/1996 | Song |
| 5,575,997 A | 11/1996 | Leung et al. |
| 5,582,834 A | 12/1996 | Leung et al. |
| 5,614,650 A | 3/1997 | Sandler et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,054,606 A | 4/2000 | Irie et al. |
| 6,069,261 A | 5/2000 | Hoffmann et al. |
| 6,096,848 A | 8/2000 | Gololobov et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,169,727 B2 | 1/2007 | Thorman |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,450,290 B2 | 11/2008 | Xu et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,678,847 B2 | 3/2010 | Yan et al. |
| 7,771,567 B2 | 8/2010 | Rives et al. |
| 7,900,558 B2 | 3/2011 | Yokoi |
| 8,119,214 B2 | 2/2012 | Schwantes et al. |
| 8,206,570 B2 | 6/2012 | Deniau |
| 8,318,060 B2 | 11/2012 | Sundberg et al. |
| 8,425,999 B2 | 4/2013 | McArdle et al. |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,249,265 B1 | 2/2016 | Stevenson et al. |
| 9,334,430 B1 | 5/2016 | Stevenson et al. |
| 9,481,640 B2 | 11/2016 | McArdle et al. |
| 2001/0005572 A1 | 6/2001 | Lobo et al. |
| 2001/0034300 A1 | 10/2001 | Yurugu et al. |
| 2002/0035231 A1 | 3/2002 | Whitehouse et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0057914 A1 | 3/2004 | Bonda et al. |
| 2004/0076601 A1 | 4/2004 | Bru-Magniez et al. |
| 2004/0082043 A1 | 4/2004 | Yadav et al. |
| 2004/0220060 A1 | 11/2004 | Bartley et al. |
| 2006/0001158 A1 | 1/2006 | Matayabas, Jr. et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 10/2007 | Malofsky et al. |
| 2007/0238872 A1 | 10/2007 | Sabesan |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0087151 A1 | 4/2009 | Benjamin et al. |
| 2009/0200652 A1 | 8/2009 | Oh et al. |
| 2009/0203861 A1 | 8/2009 | Lee et al. |
| 2009/0263604 A1 | 10/2009 | Arai et al. |
| 2009/0286433 A1 | 11/2009 | Watanabe |
| 2010/0016508 A1 | 1/2010 | Sasagawa et al. |

(56) References Cited

U.S. PATENT DOCUMENTS

| | | |
|---|---|---|
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2011/0244010 A1 | 10/2011 | Doshi |
| 2011/0255156 A1 | 10/2011 | Jethmalani et al. |
| 2012/0083523 A1 | 4/2012 | Richard et al. |
| 2012/0136130 A1 | 5/2012 | Takashima et al. |
| 2012/0203021 A1 | 8/2012 | Friese et al. |
| 2013/0019520 A1 | 1/2013 | Sello et al. |
| 2013/0281580 A1 | 10/2013 | Malofsky et al. |
| 2013/0303719 A1 | 11/2013 | Malofsky et al. |
| 2013/0324754 A1 | 12/2013 | Bredsguard |
| 2014/0058031 A1 | 2/2014 | Overbeek et al. |
| 2014/0173889 A1 | 6/2014 | Johnson et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | |
|---|---|---|
| EP | 2768917 A2 | 2/2009 |
| FR | 2788516 A1 | 7/2000 |
| GB | 432628 A | 7/1935 |
| GB | 965676 | 8/1964 |
| GB | 965767 | 8/1964 |
| GB | 975733 | 11/1964 |
| GB | 2463065 A | 3/2010 |
| JP | S56-081537 A | 7/1981 |
| JP | 63271253 A | 11/1988 |
| JP | H02281013 | 11/1990 |
| JP | H08231564 | 9/1996 |
| JP | 09258448 A | 10/1997 |
| JP | 2000199936 A | 7/2000 |
| JP | 2003201397 A | 7/2003 |
| JP | 2008174494 | 1/2007 |
| WO | 1999/046619 | 9/1999 |
| WO | 1999/055394 A1 | 11/1999 |
| WO | 2007/120630 A2 | 10/2007 |
| WO | 2010/091975 A1 | 8/2010 |
| WO | 2010/129068 A1 | 11/2010 |
| WO | 2011/059104 A1 | 5/2011 |
| WO | 2011/161045 A1 | 12/2011 |
| WO | 2012/054616 A2 | 4/2012 |
| WO | 2012/054633 A2 | 4/2012 |
| WO | 2013/059473 | 4/2013 |
| WO | 2013/066629 | 5/2013 |
| WO | 2013/149165 A1 | 10/2013 |
| WO | 2013/149168 A1 | 10/2013 |
| WO | 2013/149173 A1 | 10/2013 |

OTHER PUBLICATIONS

A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.

A. M. Vetrova et al.: "Improvement of the Thermal Stability of Cyanoacrylate Adhesives," Polymer Science, Series D, (2009), vol. 2, No. 1, pp. 27-30.

Alejandro Bugarin et al. "Efficient direct [alpha]-methylenation of carbonyls mediated by dissopropylammonium trifluoroacetate", Chemical Communications, vol. 46, No. 10 dated Jan. 25, 2010.

B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org <http://Euro.J.Org>. Chem., (2006), pp. 3767-3770.

Block, "Diethyl bis (hydroxymethyl) malonate" Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.

Corey et al. "Total Synthesis of Gibberellic Acid. A Simple Synthesiss of a Key Intermediate", J. Am. Chem. Soc. 1982, 104, 6129-6130.

Cristoph Schotes et al. "Cu(I)- and C(II)- Catalyzed Cyclo- and Michael Addition Reactions of Unsaturated [beta]-Ketoesters" The Journal of Organic Chemistry, vol. 76, No. 14 dated Jul. 15, 2011 p. 5862-5866.

G. Lai et al.: "Ionic Liquid Functionalized Silica Gel: Novel Catalyst and Fixed Solvent," Tetrahedron Letters (2006), vol. 47, pp. 6951-6953.

Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.

H, A, Oskooie et al.: "On Water: an Efficient Knoevenagel Condensation using 12-Tungstophosphoric Acid as a Reusable Green Catalyst," Synthetic Communications, (2006), vol. 36, pp. 2819-2823.

H. Hoffman et al. "Preparation and Selected Reaction of tery-Butyl 2-Methylene-3-oxoalkanoates" Chem. Ber., vol. 124 dated Jan. 1, 1991, pp. 2475-2480.

H. Jiang et al.: "Inorganic Zinc Salts Catalyzed Knoevenagel Condensation at Room Temperature without Solvent," Preparative Biochemistry & Biotechnology, (2009), vol. 39, pp. 194-200.

H. Jung et al,: "New and General Methods for the Synthesis of Arylmethylene Bis(3-Hydroxy-2-Cyclohexene-1-0nes) and Xanthenediones by EDDA and In(OTf)3-Catalyzed One-Pot Domino Knoevenagei/Michael or Koevenagei/Michaei/Cyclodehydration Reactions," Bull. Korean Chem. Soc. (2009) vol. 30, No. 9, pp. 1989-1995.

J. R. Harjani et al.: "Lewis Acidic Ionic Liquids for the Synthesis of Electrophilic Alkenes; via the Knoevenagel Condensation," Tetrahedron Letters, (2002), vol. 43, pp. 1127-1130.

J. S. Yadav et al.,: "Phosphane-Catalyzed Knoevenagel Condensation: a Facile Synthesis of a-Cyanoacrylates and a-Cyanoacrylonitriles," Eur, J, Org, Chem. (2004), pp. 546-551.

Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389 *table 2; compound 3 *.

K. Okamura and T. Date, A Facile Conversion of Ethoxydihydropyrans to 4-Cyanoethylisoxazoles, J. Heterocyclic Chem. 33, 383 (1996).

Krishna et al. "Stereodefined Access to 3-Deoxy Sugars Through a Tandem Baylis-Hillman and Lewis Acid Catalyzed Sequence", European Journal of Organic Chemistry, 2010, 813-817.

Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.

Limouzin et al., "Anionic Polymerization of n-Butyl Cyanoacrylate in Emulsion and Miniemulsion" Macromolecules, vol. 36, 2003, pp. 667-674.

M. Matziari et al. Active Methylene Phosphinic Peptides: A new Diversification Approach Organic Letters 2006 vol. 8, No. 11 pp. 2317- 2319 May 5, 2006.

M. Ware et al.: "DBU: An Efficient Catalyst for Knoeveganel Condensation under Solvent-free Condition," Bulletin of the Catalysis Society of India, (2007), vol. 6, pp. 104-106.

M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.

McCoy, M. "A New Way to Stick" Chemical & Engineering News, vol. 92, Issue 26, Jun. 30, 2014, pp. 17-18, paragraph [2].

(56) References Cited

OTHER PUBLICATIONS

P, Ballesteros et al.: "DI-tert-Butyl Methylenemalonate [Propanedioic Acid, Methylene-, bis( 1,1- dimethylethyl)ester]," Organic Syntheses. Coli. (1990), vol. 7, p. 142; (1986) vol. 64, p. 63.
P. Ballesteros et al.: "Synthesis of Di-tert-Butyl Methylenemalonate, a Sterically Hindered 1,1-Dicarbonyl Alkene," J. Ora <htto://J. Ora>. Chem, (1983), vol. 48, pp. 3603-3605.
P. Breton et al., "New Poly(Methylidudene Malonate 2.1.2) Nanoparticles: Recent Developments", Targeting of Drugs 4, NATO ASI Series, vol. 273, pp. 161-172, 1994.
P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.
P. Klemarwczyk: "A General Synthesis of 1,1 Disubstituted Electron Deficient Olefins and their Polymer Properties," Polymer,- (1998), vol. 39, No. I, pp. 173-181.
Reddy et al. "An easy-to-use heterogeneous promoted zirconia catalyst for Knoevenagel condensation in liquid phase under solvent-free conditions." Journal of Molecular Catalysts A: Chemical 258 (2006) pp. 302-307.
T. Doi et al.: "Synthesis of Dimethyl gloiosiphne a by Way of Palladium-Catalyzed Domino Cyclization," T. Ora <htto://T.Ora>. Chem., (2007), vol. 72, pp. 3667-3671.
Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
V. G. Nenajdenko et al.: "Reaction of 2-Methylene-1,3-Dicarbonyl Compounds Containing a CF3-Group with 1,3-Dienes," Tetrahedron, (2000), vol. 56, pp. 6549-6556.
Yamauchi et al. Tetrahedron Asymetry 12, (2001), 3113-3118.
Zaragoza Dorwald, Side Reactions in Organic Synthesis, 2005, Wiley-VCH Verlag GmbH & Co., KgaA, Weinheim, Preface. p. IX.
Weiss et al. Miniemulsion Polymerization as a Means to Encapsulate Organic and Inorganic Materials, Adv. Polymer Science, 2010, pp. 1-52, DOI:10.1007/12_2010_61.
Bhatia, Encapsulation of Particles Using Brittle Subterranean Applications, Thesis submitted to College of Engineering and Mineral Resources at West Virginia University in partial fulfillment of the requirements for the degree of Master of Science in Chemical Engineering, 1999.
McFarland et al, Free Radical Frontal Polymerization with a Micro-encapsulated Initiator, Macromolecules 2004, vol. 37, pp. 6670-6672.
"Comparison of the catalytic activity of MOFs and zeolites in Knoevenagel condensation", Maksym Opanasenko, et al., Catalysis Science & Technology, vol. 3 p. 500-507. (2013).
"Knoevenagel Condensation Over Acidic Zeolite", Zuo Bojun et al., Chinese Journal of Catalysis, vol. 23 (6), pp. 555-558. (2002).
"Knoevenagel reaction on a molecular sieve", Li Qifang et al., Chinese Science Bulletin, vol. 12, pp. 914-917. (1988).
"Esterification of Sludge Palm Oil Using Trifluromethanesulfonic Acid for Preparation of Biodiesel Fuel", Korean Journal of Chemical Engineering, Jun. 2013, vol. 30, issue 6, pp. 1229-1234.
Bachman et al., "Diethyl Methylenemalonate" Contirbution from the Research Laboratories of the Eastman Kodak Company, May 17, 1939, pp. 493-501.
Kütt et al., "Equilibrium Acidities of Superacids," Journal of Organic Chemistry, vol. 76, No. 2, 2011, pp. 391-395, published on the web Dec. 17, 2010.
Larras et al. Synthesis and micellization of amphiphilic poly(ethylene oxide)-block-poly(methylidene malonate 2.1.2.) diblock copolymers Macromol. Rapid Commun. dated2000, vol. 21, pp. 1089-1029.
Morrison and Boyd, *Organic Chemistry*, 4th Ed., pp. 831 and 836-8, 1983, Allyn Bacon, Inc., Boston, MA.
Olah et al., "Superelectrophilic Solvation," Accounts of Chemical Research, Apr. 2004, vol. 37, No. 4.
Otera et al., "Esterification: Methods, Reactions, and Applications", 2nd Ed., pp. 55-58, 2010, Wiley-VCH Verlag Gmbh & Co. KGaA. Weinheim, Germany.
Yamauchi et al. *A Facile Conversion of Ethoxydihydropyrans to 4-Cyanoethylisoxazoles*, Mar.-Apr. 1996, pp. 383-387.
Lee et al., "Syntheses and Toxicity of Monomers and Polymers Containing 5-Fluorouracil" J. M. S. Pure Appl. Chem. (1992), A29(2), 161-172.

\* cited by examiner

POLYMERS INCLUDING A METHYLENE BETA-KETOESTER AND PRODUCTS FORMED THEREFROM

CROSS REFERENCE TO RELATED APPLICATIONS

This application is a continuation-in-part and claims priority to U.S. patent application Ser. No. 15/363,169 filed on Nov. 29, 2016 and Ser. No. 14/868,795 filed on Sep. 29, 2015, the contents of which are each incorporated herein by reference in its entirety.

U.S. patent application Ser. No. 15/363,169 is a divisional patent application of U.S. patent application Ser. No. 14/352,406 which is a 35 U.S.C. § 371 National Phase Application of International PCT Application No. PCT/US2012/060837, filed Oct. 18, 2012 which application claims the benefit of priority to U.S. Provisional Patent Applications 61/549,092, filed Oct. 19, 2011; 61/549,104, filed Oct. 19, 2011; and 61/549,152, filed Oct. 19, 2011; each incorporated herein by reference in its entirety.

U.S. patent application Ser. No. 14/868,795 is a continuation-in-part patent application claiming priority to U.S. patent application Ser. No. 14/352,369 filed on Apr. 17, 2014, Ser. No. 14/075,334 filed on Nov. 8, 2013, and Ser. No. 14/810,741 filed on Jul. 28, 2015, each incorporated herein by reference in its entirety. U.S. patent application Ser. No. 14/352,369 is a 35 U.S.C. § 371 National Phase Application of International PCT Patent Application PCT/US2012/060840, filed on Oct. 18, 2012, which application claims the benefit of priority to U.S. Provisional Patent Applications 61/549,104, filed on Oct. 19, 2011, 61/549,092, filed on Oct. 19, 2011, and 61/549,152 filed on Oct. 19, 2011, each incorporated herein by reference in its entirety. U.S. patent application Ser. No. 14/075,334 is a continuation of U.S. patent application Ser. No. 13/880,438, filed on Jul. 22, 2013 which is a U.S. National Stage application under 35 U.S.C. § 371 of International Patent Application PCT/US2011/056903, filed Oct. 19, 2011, which International Patent Application claims the benefit of priority of U.S. Provisional Patent Applications 61/405,029, filed Oct. 20, 2010, 61/405,049, filed Oct. 20, 2010, 61/405,078, filed Oct. 20, 2010, 61/405,033, filed Oct. 20, 2010, 61/405,056, filed Oct. 20, 2010, 61/523,311, filed Aug. 13, 2011, and 61/523,705, filed Aug. 15, 2011, each incorporated herein by reference in its entirety. U.S. patent application Ser. No. 14/810,741 claims priority to U.S. patent application Ser. No. 14/789,178 filed on Jul. 1, 2015 and U.S. Provisional Patent Applications 62/186,479 filed on Jun. 30, 2015, 62/182,076 filed on Jun. 19, 2015, 62/047,283 filed on Sep. 8, 2015, and 62/047,328 filed on Sep. 8, 2015, each incorporated herein by reference in its entirety.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to a new class of methylene beta-ketoester monomers, to methods of producing or synthesizing such monomers, and to the use and application of such monomers as commercial products and compositions, including, for example, monomer-based products (e.g., inks, adhesives, coatings, sealants or reactive molding) and polymer-based products (e.g., fibers, films, sheets, medical polymers, composite polymers and surfactants).

The new monomers relate to a platform of methylene beta-ketoester monomers having the general structural formula:

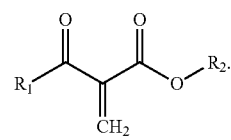

Products produced with such monomers include, for example, polymerizable compositions and polymers formed therefrom, e.g., inks, adhesives, coatings, sealants, reactive moldings, fibers, films, sheets, medical polymers, composite polymers and surfactants.

2. Background

Methylene malonate monomers have been disclosed for example in U.S. Pat. Nos. 2,313,501; 2,330,033; 3,221,745; 3,523,097; 3,557,185; 3,758,550; 3,975,422; 4,049,698; 4,056,543; 4,160,864; 4,931,584; 5,142,098; 5,550,172; 6,106,807; 6,211,273; 6,245,933; 6,420,468; 6,440,461; 6,512,023; 6,610,078; 6,699,928; 6,750,298; and Patent Publications 2004/0076601; WO/2012/054616A2; WO2012/054633A2.

As described in certain of those publications, methylene malonates have the potential to form the basis of a large-scale platform of raw materials useful in a wide variety of chemical products.

While various earlier methods for producing methylene malonates have been known for many years, these prior methods suffer significant deficiencies which preclude their use in obtaining commercially viable monomers. Such deficiencies include unwanted polymerization of the monomers during synthesis (e.g., formation of polymers or oligomers or alternative complexes), formation of undesirable side products (e.g., ketals or other latent acid-forming species which impede rapid polymerization), degradation of the product, insufficient and/or low yields, and ineffective and/or poorly functioning monomer product (e.g., poor adhesive characteristics, stability, or other functional characteristics), among other problems. The overall poorer yield, quality, and chemical performance of the monomer products formed by prior methods has impinged on their practical use in the production of the above commercial and industrial products. No viable solutions to solve the aforementioned problems have yet been proposed, accepted and/or recognized and certainly do not exist currently in the industry.

For example, in U.S. Pat. No. 2,330,033 to Gaetano D'Alelio ("the '033 patent"), methylene malonic esters are prepared by condensing a malonic ester with formaldehyde under alkaline conditions, acidifying with acetic acid and dehydrating the mass and distilling the methylene malonic ester. In each example of the '033 patent, the condensation reaction is acidified using acetic acid. Furthermore, the ester is described as polymerizing spontaneously in the absence of inhibitors. Thus, the reaction conditions described in the '033 patent would have led to the undesirable premature polymerization of the monomer and the production of deleterious side products. Further, the reference does not even recognize the formation of such deleterious side products, let alone does it provide any teachings or suggestions as to how to avoid or eliminate the formation of these impurities. Accordingly, the methylene malonates purportedly formed by this process are impractical for use in the production of viable commercial and industrial products.

Similarly, in U.S. Pat. No. 2,313,501 to Bachman et al. ("the '501 patent"), methylene dialkyl malonates are prepared by the reaction of dialkyl malonates with formaldehyde in the presence of an alkali metal salt of a carboxylic acid in a substantially anhydrous carboxylic acid solvent. The method of the '501 patent purports to provide higher yields than the prior methods of condensing formaldehyde with a dialkyl malonate in the presence of a base. In the '501 patent, methylene diethyl malonate is distilled directly from the reaction mixture under sub-atmospheric pressure. The ester is described as forming a soft waxy white polymer upon standing, indicating the presence of a high degree of deleterious side products. The '501 patent does not even recognize the formation of such deleterious side products, let alone does it provide any teachings or suggestions as to how to avoid or eliminate the formation of such impurities. Thus, the methylene malonates purportedly formed by this process are highly unstable and are impractical for use in the production of viable commercial and industrial products.

Furthermore, in U.S. Pat. No. 3,197,318 to Halpern et al. ("the '318 patent"), dialkyl methylene malonic acid esters are prepared by condensing dimethylmalonate with formaldehyde in the presence of acetic acid and an acetate of a heavy metal at 100-110° C. The reaction mixture is directly distilled under reduced pressure. The '318 patent states that in the anhydrous composition, the reaction either fails to occur or is greatly delayed by the inhibitor up to the time when the effectiveness of the inhibitor is reduced by contact of moisture therewith (from occluded surface water on glass, metal or the like). The unfavorable reaction conditions described in this reference would have led to the production of deleterious side products. The '318 patent does not even recognize the formation or presence of these impurities, let alone offer teachings or suggestions as to how to avoid or eliminate their formation. Accordingly, the methylene malonates purportedly formed by the process of the '318 patent would have been impractical for their use in the production of viable commercial products.

Also, in U.S. Pat. No. 3,221,745 to Coover et al. ("the '745 patent"), monomeric dialkyl esters of methylene malonic acid are purportedly prepared in high purity because even with small amounts of impurities that influence polymerization the adhesive utility will be impaired. The '745 patent describes removing all impurities to levels below 100 parts-per-million preferably below 10 parts-per-million. The monomers are prepared by hydrogenating the olefinic bond of a dialkyl alkoxy-methylenemalonate in the presence of a hydrogenation catalyst and pyrolyzing the reaction product. The '745 patent states that these high purity materials polymerize and form firm bonds in situ rapidly, within seconds. Indeed, the '745 patent, like related U.S. Pat. No. 3,523,097 to Coover et al. ("the '097 patent"), requires the use of an acidic stabilizer to enhance shelf-life and to prevent premature polymerization. However, the high temperature conditions of the pyrolysis reaction invariably results in the formation of unwanted and deleterious side products and is a much more expensive and difficult synthesis process for preparing methylene malonate as compared to the Knovenagel reaction with formaldehyde. Thus, the monomer purportedly formed by the processes of the '745 and '097 patents is impractical for use in the production of viable commercial and industrial products.

Still further, in U.S. Pat. No. 3,758,550 to Eck et al. ("the '550 patent") report on a general process for producing methylene malonic esters of the general formula $CH_2=C(-CO_2R)_2$, by reacting paraformaldehyde in glacial acetic acid in the presence of a catalyst to form a product in the form of a "gel" which is then "cracked" at high temperature distillation. The reaction is conducted over long periods of time, including up to 15 hours, and produces a substantial amount of deleterious side products, as evidenced by the gelatinous characteristics of the product. Further, the '550 patent contains no support showing the functionality of the monomers produced. Due to the likely presence of high levels of impurities, the functionality of the monomers produced by the '550 patent would likely be substantially compromised.

Citing numerous disadvantages of the foregoing processes, which disadvantages were said to make them difficult, if not impossible, to provide commercially viable monomers, Bru-Magniez et. al. (U.S. Pat. Nos. 4,932,584 and 5,142,098) ("the '584 and '098 patents") developed a process whereby anthracene adducts were prepared by reacting mono- or di-malonic acid ester with formaldehyde in the presence of anthracene, most preferably in a non-aqueous solvent medium in the presence of select catalysts. According to these patents, the anthracene adducts were said to be readily produced in high yields with the desired methylene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylene malonates. Despite the claim to high yields, their crude yields were generally in the range of 21-71%, and more importantly, nothing is taught with respect to the purity of the material obtained.

While the use of intermediate adducts promoted higher yields and allowed greater versatility, particularly with respect to the broader variety of methylene malonates capable of being produced, lingering problems persisted, namely batch-to-batch inconsistency and the general instability of the process as well as the so-formed crude and final products, especially in bulk storage, and of formulated products, such as adhesives, made with the same. Additionally, the adduct routes involve considerable added expense, particularly in light of the need for the additional reactants and other materials, added production steps and time, new energy requirements and environmental concerns, and the like. Furthermore, despite their advances, these processes have yet to fully or even adequately address, particularly from a commercial viability standpoint, the underlying and critical problems evidenced by the continuing inconsistency in the production of the methylidene malonates, particularly as reflected by the ongoing instability of the reaction mix particularly during the distillation and recovery of the desired product as well as of the recovered product. It is this erratic nature of the production process and resultant product and the attendant costs associated therewith that compromises and overshadows the commercial value and opportunity for these products.

Similar conclusions may be drawn from other representative prior references that purport to teach the synthesis of methylene malonates, including, for example, U.S. Pat. Nos. 3,557,185; 3,975,422; 4,049,698; 4,056,543; 4,160,864; and 6,106,807. None of these references, however, recognize the same problems discussed above, including the formation of deleterious side products, such as, ketals and other latent acid-forming species which impede monomer performance, the occurrence of unwanted polymerization (e.g., unintended formation of polymers, oligomers or alternative complexes) and the general degradation and instability of the monomer products which together substantially impedes the production of high-quality methylene malonate monomers having commercial viability.

In view of the above art, there remains no known single viable commercially suitable method or process for the chemical synthesis of methylene malonate monomers which may be utilized to produce these important raw materials for the generation of a wide variety of commercial and industrial products. Thus, a need exists for improved methods for synthesizing methylene malonate monomers that are capable of being viably used in commercial and industrial applications.

The present invention solves the aforementioned problems in the synthesis of methylene malonate monomers and paves the way to a commercially viable source of an important raw material.

Free radical polymerization of dialkyl methylene malonate monomers using heat, UV light and peroxide is described in U.S. Pat. Nos. 2,330,033 and 2,403,791, both incorporated herein by reference. In these patents, the monomer was prepared using traditional methods which results in low purity monomer. The polymer examples in these patents are all prepared via bulk polymerization. One would therefore not expect to be able to control polymer properties, such as molecular weight and molecular weight distribution.

It is envisioned that methylene beta-ketoester monomers and their associated monomeric and polymeric-based products would be useful in industrial, consumer, and medical applications. Specifically, methylene beta-ketoester monomers would provide a benefit over other monomers in that the incorporation of a ketone group adjacent to the active methylene group reduces the susceptibility of degradation of the monomer upon utilization or further functionalization. Indeed, unlike many other monomers, methylene beta-ketoester monomers and their products can be produced via sustainable routes as well as be designed to be environmentally benign, biologically benign and as such many of the products can be generally regarded as "green."

Thus, there exists a need in the art for methods of synthesizing novel methylene beta-ketoester monomers, formulating novel polymerizable compositions, and providing polymer products based on this platform.

SUMMARY OF THE INVENTION

The purpose and advantages of the present invention will be set forth in and apparent from the description that follows. Additional advantages of the invention will be realized and attained by the methods and systems particularly pointed out in the written description and claims hereof, as well as from the appended drawings.

In one aspect, the invention provides a methylene beta-ketoester monomer having a structure:

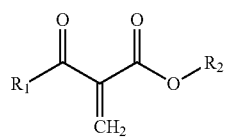

wherein $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides a method of making a methylene beta-ketoester monomer comprising:

a) reacting a beta-ketoester reactant having the structural formula:

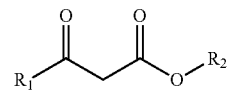

under suitable reaction conditions for sufficient time with a source of formaldehyde, optionally in the presence of an acidic or basic catalyst, and optionally in the presence of an acidic or non-acidic solvent, to form a reaction complex; and b) isolating a methylene beta-ketoester monomer from the reaction complex, wherein the methylene beta-ketoester monomer has the structural formula:

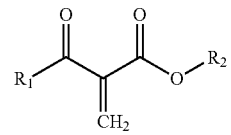

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain embodiments, the methods of the invention herein include the step of isolating the methylene beta-ketoester by:
i. contacting the reaction complex, or a portion thereof, with an energy transfer means to produce a vapor phase including the methylene beta-ketoester monomer; and
ii. collecting the methylene beta-ketoester monomer from the vapor phase.

In other embodiments, the methods of the invention herein include isolating the methylene beta-ketoester by:
i. heating the reaction complex, or a portion thereof, to a temperature between about 130° C. and about 300° C. to produce a vapor phase including the methylene beta-ketoester monomer; and
ii. collecting the methylene beta-ketoester monomer from the vapor phase.

In still other embodiments, the methods of the invention are performed under reaction conditions of:
a) an initiating temperature of between about 60° C. and about 130° C.;
b) atmospheric pressure.

In another aspect, the invention provides a method of preparing a methylene beta-ketoester monomer comprising:
a) reacting a beta-ketoester reactant having the structural formula:

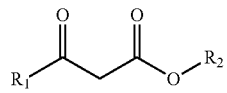

under suitable reaction conditions for sufficient time with a source of formaldehyde, optionally in the presence of an acidic or basic catalyst, and optionally in the presence of an acidic or non-acidic solvent, to form a reaction complex;
b) contacting the reaction complex, or a portion thereof, with an energy transfer means at a temperature between about 150° C. and about 300° C. to provide the reaction complex, or portion thereof, as a vapor phase; and
c) isolating a methylene beta-ketoester monomer from the reaction complex or portion thereof, wherein the methylene beta-ketoester monomer has the structural formula:

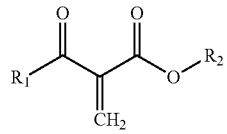

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;
or
wherein each instance of $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides a polymerizable composition comprising a methylene beta-ketoester monomer of the invention.

In certain embodiments, the polymerizable composition is capable of bonding glass to a substrate in a time period of less than about 90 seconds, less than about 60 seconds, less than about 30 seconds, or less than about 15 seconds.

In certain other embodiments, the polymerizable composition comprising a methylene beta-ketoester monomer further comprises at least one additive selected from the group consisting of an acidic stabilizer, a free radical stabilizer, a sequestering agent, a cure accelerator, a rheology modifier, a plasticizing agent, a thixotropic agents, a natural rubber, a synthetic rubbers, a filler agent and a reinforcing agent.

In another aspect, the invention provides an adhesive product comprising a methylene beta-ketoester monomer of the invention.

In certain embodiments, the adhesive products have a shelf life of at least one year.

In another aspect, the invention provides a polymer formed by polymerization of one or more methylene beta-ketoester monomers or a polymerizable composition thereof.

In certain embodiments, the polymers of the invention are useful as a sealant, a coating, a textile fiber, a water-treatment polymer, an ink carrier, a paint carrier, a packaging film, a molding, a medical polymer, a polymer film, a polymer fiber, or a polymer sheet.

In certain other embodiments, the polymers of the invention have repeat units of the formula:

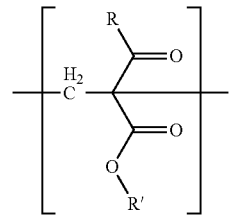

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In another aspect, the invention provides an oligomeric complex prepared by reacting a beta-ketoester with a source of formaldehyde; optionally in the presence of heat transfer agent; optionally in the presence of an acidic or basic catalyst; and optionally in the presence of an acidic or non-acidic solvent. In certain embodiments, the oligomeric complex has between 2 and 12 repeat units having the structural formula:

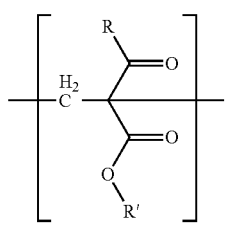

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In still another aspect, the invention provides a methylene beta-ketoester monomer prepared according to the methods of the invention.

The invention may include a step of minimizing the recovery of volatile latent acid forming impurities. This step may in certain embodiments comprise (a) adding to the reaction mixture water and an acid having a pKa range of −8 to 5; (b) adding to the reaction mixture a sterically hindered organic acid; or (c) adding to the reaction mixture a non-volatile organic acid, or any combination of (a), (b) or (c). In certain other embodiments, the step of minimizing the recovery of volatile latent acid forming impurities may comprise adding to the reaction mixture water and an acid having a pKa range of −8 to 5.

The methylene beta-ketester monomers may be used to make products, including but not limited to, an adhesive, a coating, a sealant, a composite, or a surfactant. Such products, in various embodiments, can further comprise an acidic stabilizer, a free radical stabilizer, a sequestering agent, a cure accelerator, a rheology modifier, a plasticizing agent, a thixotropic agents, a natural rubber, a synthetic rubbers, a filler agent, a reinforcing agent or a combination thereof.

In certain embodiments, the acid stabilizer can have a pKa in the range of −15 to 5, or in the range of −15 to 3, or in the range of −15 to 1.

In some embodiments, the acid stabilizer is a volatile acid stabilizer with a boiling point less than 200° C.

In other embodiments, the acid stabilizer is a volatile acid stabilizer with a boiling point less than 170° C.

In still other embodiments, the acid stabilizer is a volatile acid stabilizer with a boiling point less than 130° C.

In other embodiments, the acid stabilizer can be an acidic gas, such as, for example, $SO_2$ or $BF_3$.

In some embodiments, the acid stabilizer can be present in a concentration of about 0.1 ppm to about 100 ppm, or from about 0.1 ppm to about 50 ppm, or from about 0.1 ppm to about 25 ppm, or from about 0.1 ppm to about 15 ppm.

The methylene beta-ketoester monomers and/or products may include a free radical stabilizer, such as a phenolic free radical stabilizer, and may be present in a concentration of about 0.1 ppm to about 10000 ppm, or from about 0.1 ppm to about 3000 ppm, or from about 0.1 ppm to about 1500 ppm, or from about 0.1 ppm to about 1000 ppm, or from about 0.1 ppm to about 300 ppm, or from about 0.1 ppm to about 150 ppm.

In yet another embodiment, the present invention relates to an adhesive product or composition comprising a methylene beta-ketoester monomer prepared according to a method of the invention and which is stable for at least one year.

In other embodiments, the monomer and/or the polymerizable compositions (e.g., the adhesive products formed by a method of the invention), are compositions wherein the level of ketals is less than about 100 ppm, or less than about 50 ppm, or less than about 25 ppm, or less than about 10 ppm, or less than about 5 ppm, or even less than about 0.1 ppm, or less.

In still other embodiments, the monomer and/or the polymerizable composition (e.g., the adhesive products formed by a method of the invention), have a purity such that the level of other latent acid-forming impurities is less than about 100 ppm, or less than about 50 ppm, or less than about 25 ppm, or less than about 10 ppm, or less than about 5 ppm, or even less than about 0.1 ppm, or less.

Another aspect of the disclosure is directed at a process comprising the steps of: mixing one or more monomers (including a first monomer that is a 1,1-disubstituted alkene compound (e.g., a methylene beta-ketoester monomer)) and a solvent; adding an activator; reacting the activator with one of the one or more monomers (e.g., with the first monomer) for initiating the anionic polymerization of the one or more monomers; and anionically polymerizing the one or more monomers to form a polymer having a weight average molecular weight and/or a number average molecular weight of about 2000 daltons or more, the polymer including the first monomer, wherein the first monomer is provided as a high purity monomer having a purity of about 95 weight percent or more. Preferably the high purity monomer has a purity of about 97 weight percent, even more preferably about 99 weight percent. For example, the high purity monomer may include the 1,1-disubstituted alkene compound having an alkene group and the total concentration of any analogous compound (i.e., impurity compound) having the alkene group replaced by hydroxyalkyl group is about 3 mole percent or less (preferably about 1 mole percent or less, even more preferably about 0.1 mole percent or less, and most preferably about 0.01 mole percent or less), based on the total moles of the 1,1-disubstituted alkene compound. The 1,1, disubstituted alkene compound may be a methylene beta-ketoester monomer.

BRIEF DESCRIPTION OF THE DRAWINGS

So that those having ordinary skill in the art to which the subject invention pertains will more readily understand how to make and use the invention as described herein, preferred embodiments thereof will be described in detail below, with reference to the drawings, wherein.

DESCRIPTION OF THE INVENTION

Overview

Figure 1:
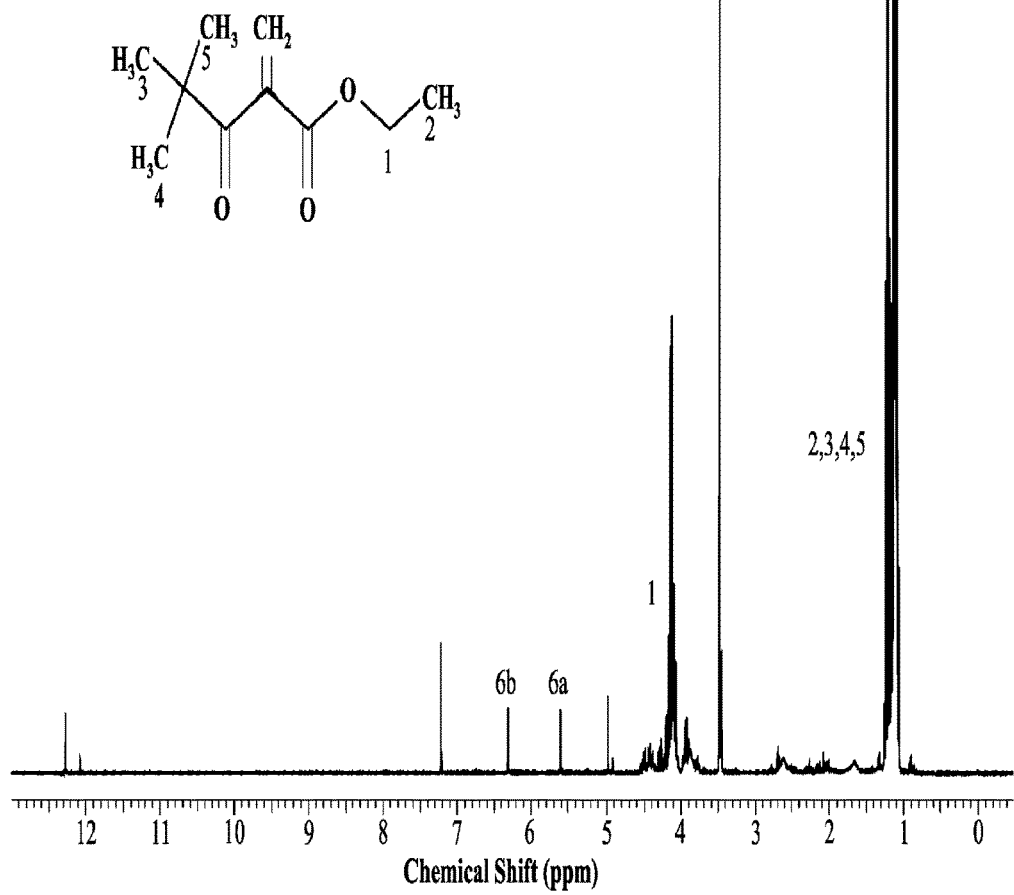
FIGS. 1 and 2 depict NMR spectra demonstrating evidence of a methylene beta-ketoester reaction product formed by the reaction of ethyl 4,4-dimethyl-3-oxopentanoate and formaldehyde.

The present invention provides new and nonobvious improvements and modifications in the use and application of the Knoevenagel reaction in order to produce methylene beta-ketoester monomers:

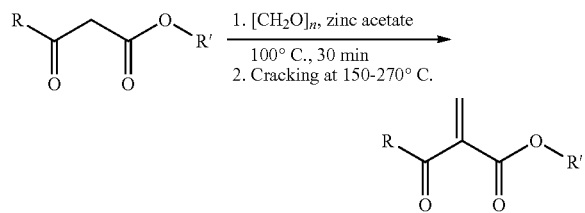

Modified Knoevenagel Reaction

While the above reaction scheme shows a direct condensation reaction, it has been discovered that an intermediary species (oligomeric complex) may be formed in certain instances. The oligomeric complex may then be cracked to yield the monomer product. As those having skill in the art will appreciate, the reaction scheme may also yield side reactions and undesired products, and unreacted starting material from which the methylene beta-ketoester monomers are subsequently isolated.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "methylene beta-ketoester monomer" refers to a compound having the core formula —C(O)—C(=CH$_2$)—C(O)O—.

As used here, the term "beta-ketoester" refers to a compound having the core formula —C(O)—CH$_2$—C(O)O—.

As used herein, the term "monofunctional" refers to a methylene beta-ketoester or a beta-ketoester having only one core formula.

As used herein, the term "difunctional" refers to a methylene beta-ketoester or a beta-ketoester having two core formulas.

As used herein, the term "multifunctional" refers to a methylene beta-ketoester or a beta-ketoester having two or more core formulas. Thus the term multifunctional encompasses the term difunctional.

As used herein, the term "reaction complex" refers to the materials which result after reacting a beta-ketoester starting material with a source of formaldehyde. Such reaction complexes may comprise, without limitation, methylene beta-ketoester monomers, oligomeric complexes, irreversible complex impurities, starting materials, or latent acid-forming impurities.

As used herein, the term "reaction vessel" refers to any container in which the reactants, solvents, catalysts or other materials may be combined for reaction. Such reaction vessels can be made of any material known to one of skill in the art such as metal, ceramic or glass.

As used herein, the term "vapor phase" refers to a gaseous phase which may comprise, without limitation, vaporized methylene beta-ketoester monomer, vaporized starting materials; vaporized solvents, or vaporized impurities.

As used herein, the term "recovering" or "obtaining" or "isolating" refers to the removal of the monomer from the reaction mixture, vapor phase, or condensed vapor phase by one of the methods described herein, although the desired product may not be in a purified form. The term "crack" is also used to indicate depolymerization of an oligomeric complex. The desired methylene beta-ketoester monomer may be obtained by "cracking" an oligomeric complex found in the reaction complex.

As used herein, the term "sterically hindered" refers to a compound in which the size of groups within the molecule prevents chemical reactions that are observed in related smaller molecules.

As used herein, the terms "volatile" and "non-volatile" refers to a compound which is capable of evaporating readily at normal temperatures and pressures, in the case of volatile; or which is not capable of evaporating readily at normal temperatures and pressures, in the case of non-volatile.

As used herein, the term "energy transfer means" refers to a means which is capable of volatizing a reaction complex, usually by, but not limited to, rapidly heating the reaction complex to temperatures from about 150° C. to about 300° C. Such energy transfer means include, but are not limited to, heat transfer agents, heat transfer surfaces, lasers, and sources of radiation.

As used herein, the term "heat transfer agent" refers to a material which is capable of achieving a high temperature and transferring that temperature to a reaction mixture. Such heat transfer agents are typically able to reach temperatures from about 150° C. to about 300° C. and include, but are note limited to silica, silicone oil, mineral oil, a petroleum based heat transfer oil or a synthetic chemical based heat transfer oil. In certain embodiments, the heat transfer agent can be pre-formed reaction complex.

As used herein the term "pre-formed reaction complex" refers to a reaction complex as defined herein which is prepared by reacting step (a) as described herein in advance of the vaporization step (b). Such pre-formed reaction complexes can be formed up to a year, up to six months, up to 3 months, up to 1 month, up to 2 weeks, up to 1 week, up to 3 days, or up to 1 day in advance of the vaporization step (b). In such instances, the vaporization step (b) is performed on a newly prepared reaction complex. In certain aspects the pre-formed reaction complex can refer to an oligomeric complex as defined herein.

As used herein the term "substantial absence" as in "substantial absence of acidic solvent" refers to a reaction mixture comprising less than 1% by weight of the particular component as compared to the total reaction mixture. In certain embodiments, a "substantial absence" refers to less than 0.7%, less than 0.5%, less than 0.4%, less than 0.3%, less than 0.2% or less than 0.1% by weight of the of the particular component as compared to the total reaction mixture. In certain other embodiments, a "substantial absence" refers to less than 1.0%, less than 0.7%, less than 0.5%, less than 0.4%, less than 0.3%, less than 0.2% or less than 0.1% by volume of the of the particular component as compared to the total reaction mixture.

As used herein, the term "stabilized," e.g., in the context of "stabilized" molecules of the invention or compositions comprising same, refers to the tendency of the molecules of the invention (or their compositions) to substantially not polymerize with time, to substantially not harden, form a gel, thicken, or otherwise increase in viscosity with time, and/or to substantially show minimal loss in cure speed (i.e., cure speed is maintained) with time.

As used herein, the term "shelf-life," e.g., as in the context of the molecules of the invention having an improved "shelf-life," refers to the molecules of the invention which are stabilized for a given period of time, e.g., 1 month, 6 months, or even 1 year or more.

As used herein, the term "latent acid-forming impurities" or "latent acid-forming impurity" refers to any impurity that, if present along with the recovered monomer, will with time be converted to an acid. The acid formed from these impurities tends to result in overstabilization of the monomer (e.g., methylene beta-ketoester monomer or methylene malonate monomer), thereby reducing the overall quality and reactivity of the monomer.

As used herein, the term "ketal" refers to molecule having a ketal functionality; i.e. a or molecule containing a carbon bonded to two —OR groups, where O is oxygen and R represents any alkyl group.

Description of Exemplary Embodiments

Methylene beta-ketoester monomers in accordance with the present invention may be made by a modified Knoevenagel condensation reaction of a beta-ketoester with formaldehyde under suitable reaction conditions. The general reaction scheme is provided below.

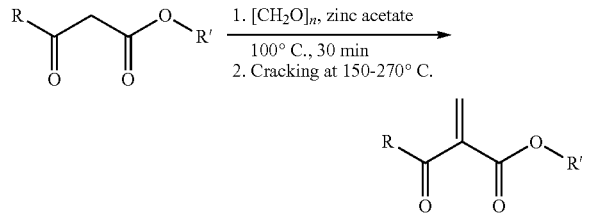

Modified Knoevenagel Reaction

Methylene Beta-ketoester Monomers

In one aspect, the invention provides a methylene beta-ketoester monomer having the structural formula:

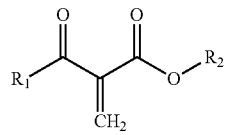

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain embodiments, the invention provides a methylene beta-ketoester monomer having the structural formula:

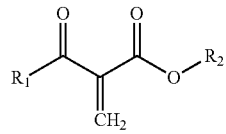

wherein each instance of $R_1$ and $R_2$ are independently $C_1$-$C_6$ alkyl, halo-($C_1$-$C_6$ alkyl), $C_3$-$C_6$ cycloalkyl, heterocyclyl, heterocyclyl-($C_1$-$C_6$ alkyl), aryl, aryl-(C1-C6 alkyl), heteroaryl or heteroaryl-($C_1$-$C_6$ alkyl), each of which may be optionally substituted by halo or $C_1$-$C_6$ alkoxy.

In other embodiments, the invention provides a methylene beta-ketoester monomer having the structural formula:

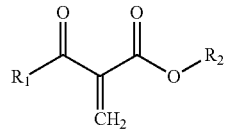

wherein each instance of $R_1$ and $R_2$ are independently $C_1$-$C_6$ alkyl or aryl.

Reactants

The reaction for making methylene beta-ketoester monomers of the invention includes at least two basic reactants: a beta-ketoester precursor and a source of formaldehyde.

The methylene beta-ketoester precursors in accordance with exemplary embodiments disclosed herein include beta-ketoesters able to undergo a condensation reaction at the alpha carbon. Beta-ketoester precursors include, but are not limited to, molecules having the structural formula:

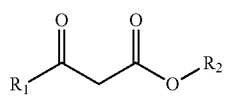

wherein each instance of $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; or wherein $R_1$ and $R_2$ are taken together with the atoms to which they are bound to form a 5-7 membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

In certain other embodiments, the present invention contemplates the following specifically identified beta-ketoester precursors: ethyl 4,4-dimethyl-3-oxopentanoate, ethyl 3-oxo-3-phenylpropanoate, ethyl 3-oxohexanoate, ethyl 3-oxobutanoate, methyl 3-oxobuanoate, ethyl 4-methyl-3-oxopentanoate, and ethyl 3-oxopenanoate among others.

The beta-ketoester precursor may be derived or obtained from any source, including any commercial source, derived from nature, other compounds, synthesized by other processes, etc. In certain embodiments, the beta-ketoester precursors are obtained from "green" sources. For example, the beta-ketoester precursors can be derived from biological sources, such as via fermentation production systems whereby microorganisms generate the beta-ketoester precursors is direct metabolic by-products of fermentation—or whereby the microorganisms generate metabolic by-products of fermentation that can be then converted inexpensively to the desired beta-ketoester precursors. These fermentation production systems are well-known in the art and may utilize either—or both—microorganisms derived from nature or engineered microorganisms that are specifically designed to produce the desired beta-ketoester precursors products, e.g., recombinant or engineered *Escherichia coli*. The beta-ketoester precursor is reacted with a source of formaldehyde. The methods of the invention also contemplate any suitable source of formaldehyde. For example, the formaldehyde may be synthesized, derived from another chemical species (e.g., paraformaldehyde), or obtained from nature or from some other suitable source. In certain embodiments, the formaldehyde is introduced in the form of a gas. Commercial sources of formaldehyde and paraformaldehyde are readily available, which may include, for example, trioxane and formalin (e.g., aqueous formaldehyde). The source of formaldehyde may be paraformaldehyde, formalin or gaseous formaldehyde. In certain embodiments, the formaldehyde is obtained from paraformaldehyde. In an exemplary embodiment, the source of formaldehyde is paraformaldehyde that is thermally degraded to formaldehyde in the reaction vessel. It is envisioned that other means of providing formaldehyde to the reaction vessel may be utilized, for example, a stream of gaseous formaldehyde.

Catalysts

In an certain embodiments, the methods of preparing the methylene beta-ketoester takes place in the presence of a suitable catalyst. However, it is envisioned that certain reactions may not required the presence of a catalyst.

In certain embodiments, the catalysts that may be used include, but are not limited to, basic catalysts such as potassium acetate, sodium acetate, zinc acetate, zinc diacetate dihydrate, aluminum acetate, calcium acetate, magnesium acetate, magnesium oxide, copper acetate, lithium acetate, aluminum oxide, or zinc oxide.

In further embodiments, the catalysts include, but are not limited to, acidic catalysts such as paratoluene sulfonic acid, dodecylbenzene sulfonic acid, boron trifluoride, zinc perchlorate, sulfated zirconium oxide, sulfated titanium oxide, lithium chloride, boron trifluoride etherate, ferric sulfate, zirconium oxychloride, cupric chloride, titanium tetrachloride, or zinc chloride.

Still other exemplary catalysts are heterogeneous catalysts. Still other exemplary catalysts are enzyme catalysts. An exemplary enzyme is Novozym® 435 available from Novozyme. Novozym 435 is an immobilized granulate, non-specific lipase particularly useful for ester production. Neutral catalysts can also include silica and other insoluble surface-active agents.

In still further embodiments, amphoteric catalysts can include, but are not limited to, aluminum oxide, aluminum acetate, zinc acetate, magnesium acetate, and zinc oxide.

In still other embodiments, the present inventors have surprisingly and unexpectedly found that no catalyst is required to conduct the synthesis reaction of the invention. Specifically, in this embodiment, the reaction can be conducted with all of the reactants added to the reaction vessel at the start of the reaction prior to adding heat. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

Solvents

The present invention contemplates that the synthesis reaction include an acidic or non-acidic solvent, or optionally no solvent at all.

Non-acidic solvents can include, but are not limited to, tetrahydrofuran, chloroform, dichloromethane, toluene, heptane, ethyl acetate, n-butyl acetate, dibutyl ether and hexane.

Acidic solvents can include, but are not limited to acetic acid and propionic acid.

In certain embodiments, the acidic solvent is added just prior to recovery.

In certain other embodiment, optionally no solvent is needed. This zero-solvent approach will not only decrease the overall cost of production but will also help to lessen any negative impact on the environment caused by the methods of the invention, i.e., provides an environmentally-friendly approach to the synthesis of 2-methylene-1,3-disubstituted-propane-1,3-diones. An advantage of this condition is the avoidance or minimization of the formation of impurities, e.g., ketals and other latent acid-forming species.

In still other embodiments, the present inventors have surprisingly and unexpectedly found that the synthesis reaction of the invention may be conducted in the absence of both a solvent and a catalyst. Specifically, in this embodiment, the reaction can be conducted with all of the reactants added to the reaction vessel at the start of the reaction prior to adding heat and in the absence of a solvent. The source of formaldehyde in this embodiment is preferably solid paraformaldehyde, and is added along with the other reactants, including the malonic ester, prior to adding heat. This reaction surprisingly can be run rapidly and in a continuous mode and unexpectedly avoids the formation of—or substantially minimizes the formation of—deleterious side products, unwanted polymerization complexes and degradation of the monomer products.

The formation of the monomer may be carried out with a step of minimizing the recovery of volatile latent acid forming impurities from the reaction complex, such as ketals, which can co-distill with the 1,1-disubstituted alkene monomer (e.g., methylene beta-ketoester monomer or methylene malonate monomer) products and then revert to their acidic form with time. Once in their acidic form, the acidic environment increases, which further blocks or weakens the reactivity of the 1,1-disubstituted alkene monomer as they are stabilized against polymerization. This can be particularly relevant to the use of 1,1-disubstituted alkene monomers in the context of adhesives, where the increased acid content with time due to the presence of such volatile latent acid forming impurities can impinge on the overall reactivity and cure speed, etc., of the monomer products.

Although the invention may employ an improved Knovenagel reaction with formaldehyde to synthesize 1,1-disubstituted alkene monomer (e.g., methylene beta-ketoester monomer or methylene malonate monomer), the present invention should not be limited as such. The present inventors have generally recognized it is believed for the first time general concept that the performance and overall quality of 1,1-disubstituted alkene monomer (e.g., methylene beta-ketoester monomer or methylene malonate monomer) is particularly sensitive to the presence of unwanted alternative and deleterious side products and unwanted monomer degradation and/or consumption is widely applicable to any type of synthesis that can be used to generate 1,1-disubstituted alkene monomer. Prior to the present invention, the significance and nature of these types of impurities and their effects on the performance and quality of methylene malonates was not previously contemplated. Thus, for the first time, the present invention provides a viable approach to producing 1,1-disubstituted alkene monomer(s) that can be utilized as the basis for viable consumer and industrial monomer-based (e.g., adhesives) and polymer-based (e.g., fibers) products.

The 1,1-disubstituted alkene compound (e.g., the methylene beta-ketoester compound) preferably is prepared using a method which results in a sufficiently high purity so that it can be polymerized. The purity of the 1,1-disubstituted alkene compound (e.g., the methylene beta-ketoester compound) may be sufficiently high so that 70 mole percent or more, preferably 80 mole percent or more, more preferably 90 mole percent or more, even more preferably 95 mole percent or more, and most preferably 99 mole percent or more of the 1,1-disubstituted alkene compound is converted to polymer during a polymerization process. The purity of the 1,1-disubstituted alkene compound (e.g, the methylene beta-ketoester compound) preferably is about 85 mole percent or more, more preferably about 90 mole percent or more, even more preferably about 93 mole percent or more, even more preferably about 95 mole percent or more, even more preferably about 97 mole percent or more, and most preferably about 99 mole percent or more, based on the total weight of the 1,1-disubstituted alkene compound. If the 1,1-disubstituted alkene compound includes impurities, preferably about 40 mole percent or more, more preferably about 50 mole percent or more of the impurity molecules are the analogous 1,1-disubstituted alkane compound. The concentration of any impurities having a dioxane group preferably is about 2 mole percent or less, more preferably about 1 mole percent or less, even more preferably about 0.2 mole percent or less, and most preferably about 0.05 mole percent or less, based on the total weight of the 1,1-disubstituted alkene compound. The total concentration of any impurity having the alkene group replaced by an analogous hydroxyalkyl group (e.g., by a Michael addition of the alkene with water), preferably is about 3 mole percent or less, more preferably about 1 mole percent or less, even more preferably about 0.1 mole percent or less, and most preferably about 0.01 mole percent or less, based on the total moles in the 1,1-disubstituted alkene compound. Preferred 1,1-disubstituted alkene compounds are prepared by a process including one or more (e.g., two or more) steps of distilling a reaction product or an intermediate reaction product (e.g., a reaction product or intermediate reaction product of a source of formaldehyde and a malonic acid ester).

The 1,1-disubstituted alkene compound (e.g., the methylene beta-ketoester compound) may include a monomer produced according to the teachings of U.S. Pat. No. 8,609,885 (Malofsky et al.) incorporated herein by reference in its entirety. Other examples of monomers which may be employed include the monomers taught in International Patent Application Publication Nos. WO2013/066629 and WO 2013/059473, both incorporated herein by reference.

Stabilization

Certain embodiments of the present invention provide monomers that are amenable to anionic polymerization. Therefore, to prevent unwanted polymerization and extend shelf life, certain exemplary embodiments include suitable acidic stabilizers, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Reaction Conditions

In certain embodiments of the present invention, the starting precursor is reacted with paraformaldehyde in the presence of a catalyst (e.g., zinc acetate dehydrate) at 60° C.-130° C. (e.g., 100° C.) for at least about 30 minutes. The resulting intermediate material (e.g., oligomeric complex) is then thermally depolymerized to the vinyl containing product by addition to a hot surface set from 150° C. to 270° C. The resulting crude monomer is then purified, for example by distillation, fractional distillation or other separation methods.

For a typical lab scale reaction: a 3-neck 250 mL round bottom reaction flask was equipped with an overhead stirrer, a heating mantle, and a temperature probe connected to a temperature controller. The reaction flask was adequately vented to the back of the hood to reduce the possibility of pressure build-up. The beta-ketoester (precursor), paraformaldehyde (1.8 equiv) and zinc acetate (0.001 equiv) were added to the reaction flask. The contents of the flask were mixed for approximately 2 minutes prior to the application of heat. After the initial mixing period the temperature controller was set to 100° C. The heterogeneous reaction mixture was allowed to heat with the temperature for dissolution and onset of exotherm being noted. Once a rapid increase in temperature was observed, heating was discontinued. Once the exotherm subsided, the heating mantle was immediately removed and the reaction mixture (herein "reaction complex") was allowed to cool to room temperature to afford the oligomeric mixture.

To isolate the methylene beta-ketoester monomer from the reaction complex, a 4-neck suitable round bottom flask was equipped with a mechanical stirrer, heating mantle, a thermocouple connected to a temperature controller, an addition funnel, a Claisen adapter, and a vacuum adapter connected to a receiver one-neck round bottom flask which was placed in an ice-bath. The system was evacuated to low pressure (1-250 mmHg). The oligomeric mixture was added to the addition funnel. The reaction flask was then applied via the connected heating mantle to 150-270° C. Once the temperature inside the flask reached the desired range, a drop-wise addition of the oligomer (reaction complex) to reaction flask was started. The addition rate was maintained so that the set temperature was maintained in the desired range. After the addition was complete, the heating mantle was turned off and the system was allowed to cool to room temperature, at this point the system was opened to atmospheric pressure. An aliquot was then taken for analysis and the remaining cracked distillate was either distilled further via fractional distillation to improve purity or placed in a refrigerator.

This general reaction scheme was utilized to provide the examples provided herein. Due to the wide variety of example obtained, it is envisioned that this general reaction scheme can be utilized to provide a wide array of methylene beta-ketoester monomers as set forth herein. Further, it is envisioned that modifications can be made to this general reaction scheme in order to improve efficiencies and purity of the product obtained.

Methods of Synthesis

In another aspect, the invention provides a method of preparing methylene beta-ketoester monomers according to the reaction scheme disclosed herein.

In certain embodiments, the method for preparing the methylene beta-ketoester monomers comprises:

a) reacting a beta-ketoester reactant having the structural formula:

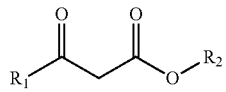

under suitable reaction conditions for sufficient time with a source of formaldehyde, optionally in the presence of an acidic or basic catalyst, and optionally in the presence of an acidic or non-acidic solvent, to form a reaction complex; and b) isolating a methylene beta-ketoester monomer from the reaction complex, wherein the methylene beta-ketoester monomer has the structural formula:

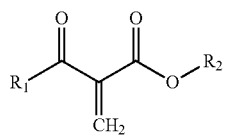

wherein $R_1$ and $R_2$ are defined above.

In certain embodiments, the reaction may be initiated at temperatures between about 60° C. to about 130° C., at atmospheric pressure. It is contemplated that the reaction conditions may be modified depending on the source of formaldehyde. For example, when paraformaldehyde is utilized within the reaction vessel, the initial temperature must be high enough to make free formaldehyde available for the reaction. If another source of formaldehyde is utilized, those having skill in the art will appreciate that the reaction conditions may be modified accordingly. Exemplary sources include paraformaldehyde, formalin, trioxane, gaseous formaldehyde, or any reaction or process in which formaldehyde is liberated.

In other embodiments, the methylene beta-ketoester monomer may be isolated from the reaction complex by contacting the reaction complex, or a portion thereof, with an energy transfer means to produce a vapor phase including the methylene beta-ketoester monomer; and collecting the methylene beta-ketoester monomer from the vapor phase.

In still other embodiments, the methylene beta-ketoester monomer may be isolated from the reaction complex immediately, or the reaction complex may be stored, preferably refrigerated, until a later time. In an exemplary embodiment, the reaction complex is not acid stabilized prior to isolating the methylene beta-ketoester monomer.

In other embodiments, the reaction complex, or a portion thereof, may be heated to a vapor phase and condensed in order to isolate the methylene beta-ketoester monomer. The reaction complex may be heated to a temperature between about 130° C. and about 300° C.

In still other embodiments, the reaction complex, or a portion thereof, may come in contact with an energy transfer means in order to facilitate isolation of the monomer. In an exemplary embodiment, the reaction complex, or portion thereof, may be vaporized in a very short time, for example less than 15 minutes, preferably less than 1 minute, more preferably less than 30 seconds, and less than 1 second. Certain exemplary embodiments contemplate vaporizing the reaction complex in a continuous manner as it is formed during the reaction step.

Exemplary energy transfer means include a heat transfer agent, a heat exchanger, a laser, microwave energy, sonic energy, electromagnetic energy, and a source of radiation, or any combination thereof. The energy transfer means operates to quickly vaporize the reaction complex (or portion thereof) to permit isolation of the monomer product. For example, an oligomeric complex may be formed, and the energy transfer means is utilized to "crack" or depolymerize the oligomer to allow isolation of the monomer. In certain embodiments, the oligomeric complex may include oligomers of 2-12 units able to provide monomer product upon crack.

In certain exemplary embodiments, the heat transfer agent is a heated inert gas, one or more metal beads, one or more glass beads, one or more porcelain beads, sand, silica, silicone oil, mineral oil, a petroleum based heat transfer oil, a synthetic chemical based heat transfer oil, or a pre-formed portion of the reaction complex.

In certain other embodiments, the heat exchanger is a shell and tube heat exchanger, a plate heat exchanger, and adiabatic wheel heat exchanger, a finned pipe heat exchanger, a plate fin heat exchanger, or a scraped surface heat exchanger.

In still other embodiments, the vapor phase of the reaction complex is condensed, and the condensate is subject to one or more further separation processes. For example, the separation process may include any of simple distillation, fractional distillation, flash distillation, steam distillation, vacuum distillation, short path distillation, thin-film distillation, reactive distillation, pervaporation, extractive distillation, flash evaporation, rotary evaporation, liquid/liquid extraction, centrifuging, or any combination thereof, and other techniques known to those having skill in the art.

Compositions

The methylene beta-ketoester monomers of the invention can be incorporated into any number of compositions and products including but not limited to reactive monomer-based compositions, reactive oligomer-based compositions and reactive polymer-based compositions.

Exemplary compositions can be analyzed by placing a drop of a monomer composition on a substrate (for example a glass slide or 4"×1" polycarbonate sample). Another glass slide or piece of polycarbonate is pressed on top over the monomer-covered area. The time is then immediately recorded from pressing the top-slide till the two slides are bonded tightly. In such embodiments, the exemplary composition is capable of bonding glass to a substrate in less than about 90 seconds, less than about 60 seconds, less than about 30 seconds or less than about 15 seconds. Similarly, the exemplary composition is capable of bonding polycarbonate to a substrate in less than about 90 seconds, less than about 60 seconds, less than about 45 seconds or less than about 30 seconds.

Alternatively, exemplary compositions can be analyzed by mixing 0.5 ml of monomer with 0.3 ml of 3% tertiary butyl ammonium fluoride (TBAF) in Dibutyl Phthalate solution. The time is recorded from adding the TBAF solution till the mixture become solid with vigorous stirring or mixing. In such embodiments, said composition solidifies upon addition of 3% tertiary butyl ammonium fluoride (TBAF) in Dibutyl Phthalate solution in less than about 15 seconds, less than about 10 seconds, or less than about 7 seconds.

Alternatively still, the exemplary compositions can be analyzed by placing 0.5 ml of monomer into a test tube and cap with a cork stopper and keeping the test tubes containing monomers at 25° C., or in ovens at 55° C. or 82° C. In each case the storage stability test is performed at atmospheric pressure. Time is recorded when the monomer became a gel or solid. In such embodiments, said composition remains stable at 25° C. and at atmospheric pressure for more than 10 days, more than 15 days, more than 20 days, more than 25 days or more than 30 days. Similarly, said composition remains stable at 82° C. and at atmospheric pressure for more than about 2 hours, more than about 3 hours, or more than about 4 hours.

Exemplary compositions include, but are not limited to an adhesive, a coating, a sealant, a composite, or a surfactant.

Additionally polymer products include, but are not limited to, a sealant, a thermal barrier coating, a textile fiber, a water-treatment polymer, an ink carrier, a paint carrier, a packaging film, a molding, a medical polymer, a polymer film, a polymer fiber or a polymer sheet.

In each case, the exemplary compositions may be formulated to include one or more materials to extend the shelf-life as well as control the onset of cure of the materials. In certain embodiments, the compositions are formulated such that the composition is stable for at least 1 month, or for at least 2 months, or for at least 3 months, or for at least 4 months, or for at least 5 months, or for at least 5-10 months, or for at least 10-20 months, or for at least 20-30 months. Preferably, the adhesive composition comprising the methylene beta-ketoester monomers or other commercial compositions or products, are stable for at least one year.

Such formulation materials include acidic stabilizer, volatile acid stabilizers, acidic gases, free radical stabilizers, sequestering agents, cure accelerators and rheology modifiers.

Exemplary embodiments contemplate any suitable acidic stabilizer known in the art, including, for example, trifluoromethane sulfonic acid, maleic acid, methane sulfonic acid, difluoro acetic acid, trichloroacetic acid, phosphoric acid, dichloroacetic acid, chlorodifluoro or like acid. Acidic stabilizers can include any material which can be added to the monomer or polymer compositions to extend shelf-life, e.g., by up to, for example, 1 year or more. Such acidic stabilizers may have a pKa in the range of, for example, between about −15 to about 5, or between about −15 to about 3, or between about −15 to about 1, or between −2 to about between about −2 to about 2, or between about 2 to about 5, or between about 3 to about 5.

Volatile acid stabilizers include any material which can be added to the monomer or polymer compositions to extend shelf-life and stabilize the vapor phase above the composition upon storage, e.g., acidic gases. Such volatile acid stabilizers may have a boiling point, for example, less than about 200° C.; less than about 170° C.; or less than about 130° C.

Acidic gases include any gaseous material which can be added to the monomer or polymer compositions to extend shelf-life and stabilize the vapor phase above the composition upon storage. Such acid gases can include, but are not limited to, $SO_2$ or $BF_3$.

For each of these acidic stabilizing materials, such acidic stabilizer can be present in a concentration of about 0.1 ppm to about 100 ppm; about 0.1 ppm to about 25 ppm; or about 0.1 ppm to about 15 ppm.

Free radical stabilizers can include any material capable of stabilizing or inhibiting free radical polymerization of the material upon standing. In one embodiment, the free radical stabilizers are phenolic free radical stabilizers such as, HQ (hydroquinone), MEHQ (methyl-hydroquinone), BHT (butylated hydroxtoluene) and BHA (butylated hydroxyanisole). In certain embodiments, the free radical stabilizers are present in a concentration of 0.1 ppm to 10,000 ppm; 0.1 ppm to 3000 ppm; or 0.1 ppm to 1500 ppm. In certain other embodiments, particularly where a free radical or ultraviolet cure will be utilized, the free radical stabilizers are present in a concentration of 0.1 ppm to 1000 ppm; 0.1 ppm to 300 ppm; or 0.1 ppm to 150 ppm.

Sequestering agents include any material capable of enhancing the bonding of materials containing acid salts such as paper or wood. Such sequestering agents include, but are not limited to crown ethers, silyl crowns, calixarenes and polyethylene glycols. Sequestering agents also enhance the utility of surface accelerators that are acid salts applied to surfaces to control the rate of cure of the materials.

Cure accelerators include any material capable of speeding the rate of cure of the methylene beta-ketoester monomers. Cure accelerators also include any material capable of speeding the cure through volume of the applied composition. Such cure accelerators include but are not limited to sodium or potassium acetate; acrylic, maleic or other acid salts of sodium, potassium lithium copper and cobalt; salts such as tetrabutyl ammonium fluoride, chloride, or hydroxide; or chemically basic materials such as amines and amides, or salts of polymer bond acids, benzoate salts, 2,4-pentanedionate salts, sorbate salts, or propionate salts. Such cure accelerators can be added directly to the exemplary compositions or applied to the material to be bonded prior to addition of the composition.

Rheology modifiers include any material which can modify the viscosity of the exemplary compositions as well as thixotropic properties for greater utility in certain applications. Rheology modifiers include, but are not limited to, hydroxyethylcellulose, ethyl hydroxyethylcellulose, methylcellulose, polymeric thickeners, pyrogenic silica or a combination thereof.

In certain embodiments, the exemplary compositions may include tougheners. Such tougheners include, but are not limited to, acrylic rubbers; polyester urethanes; ethylene-vinyl acetates; fluorinated rubbers; isoprene-acrylonitrile polymers; chlorosulfonated polyethylenes; homopolymers of polyvinyl acetate; and reaction products of the combination of ethylene, methyl acrylate and monomers having carboxylic acid cure sites, which once formed are then substantially free of processing aids and anti-oxidants; and combinations thereof. In certain embodiments, the tougheners include those disclosed in U.S. Pat. No. 4,440,910 (O'Connor), directed to rubber toughened cyanoacrylate compositions through the use of certain organic polymers as toughening additives that are elastomeric, i.e., rubbery, in nature, such as acrylic rubbers; polyester urethanes; ethylene-vinyl acetates; fluorinated rubbers; isoprene-acrylonitrile polymers; chlorosulfonated polyethylenes; and homopolymers of polyvinyl acetate. In certain embodiments, the toughener is an elastomeric polymer which is a copolymer of methyl acrylate and ethylene, manufactured by DuPont, under the name of VAMAC, such as VAMAC N123 and VAMAC B-124. VAMAC N123 and VAMAC B-124 are reported by DuPont to be a master batch of ethylene/acrylic elastomer. In other embodiments, the toughener may be the DuPont materials called VAMAC B-124, N123, VAMAC G, VAMAC VMX 1012 or VCD 6200. In other instances, the toughener may be a rubber toughening component having (a) reaction products of the combination of ethylene, methyl acrylate and monomers having carboxylic acid cure sites, (b) dipolymers of ethylene and methyl acrylate, and combinations of (a) and (b), which once the reaction products and/or dipolymers are formed are then substantially free of processing aids, such as the release agents octadecyl amine (reported by DuPont to be available commercially from Akzo Nobel under the tradename ARMEEN 18D), complex organic phosphate esters (reported by DuPont to be available commercially from R.T. Vanderbilt Co., Inc. under the tradename VANFRE VAM), stearic acid and/or polyethylene glycol ether wax, and anti-oxidants, such as substituted diphenyl amine (reported by DuPont to be available commercially from Uniroyal Chemical under the tradename NAUGARD 445). Commercial examples of such rubber tougheners include VAMAC VMX 1012 and VCD 6200 rubbers, and these may be used too.

The exemplary compositions containing methylene beta-ketoester monomer may also optionally include other additives, such as plasticizing agents, thixotropic agents, natural or synthetic rubbers, filler agents, and reinforcing agents, etc. Such additives are well known to those skilled in the art.

The exemplary compositions containing methylene beta-ketoester monomer may optionally include at least one plasticizing agent that imparts flexibility to the polymer formed from the methylene beta-ketoester monomer. The plasticizing agent preferably contains little or no moisture and should not significantly affect the stability or polymerization of the monomer. Such plasticizers are useful in polymerized compositions to be used in any application in which flexibility of the adhesive or polymer product is desirable.

Examples of suitable plasticizers include, without limitation, acetyl tributyl citrate, dimethyl sebacate, triethyl phosphate, tri (2-ethylhexyl)phosphate, tri (p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts less than about 60 weight %, or less than about 50 weight %, or less than about 30 weight %, or less than about 10 weight %, or less than about 5 weight %, or less than about 1 weight % or less, provides increased film strength (e.g., toughness) of the polymerized monomer over polymerized monomers not having plasticizing agents.

The exemplary compositions containing methylene beta-ketoester monomer may also optionally include at least one thixotropic agent, i.e., the property of exhibiting a high fluidity during deformation by force of a sprayer, roller or trowel, but losing the fluidity when left at rest. Suitable thixotropic agents are known to the skilled artisan and include, but are not limited to, silica gels such as those treated with a silyl isocyanate. Examples of suitable thixotropic agents are disclosed in, for example, U.S. Pat. Nos. 4,720,513 or 4,510,273, the disclosures of which are hereby incorporated in their entireties.

The exemplary compositions containing methylene beta-ketoester monomer may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The exemplary compositions containing methylene beta-ketoester monomer may also optionally comprise one or more other reinforcing agents (e.g., fibrous reinforcements) other than natural or synthetic rubber to impart impact resistance and/or to impart structural strength or to provide shape or form. Examples of such agents are well known in the art. Examples of suitable fibrous reinforcement include PGA microfibrils, collagen microfibrils, cellulosic microfibrils, and olefinic microfibrils. The compositions may also contain colorants such as dyes, pigments, and pigment dyes. Examples of suitable colorants include 6-hydroxy-5-[(4-sulfophenyl)axo]-2-naphthalene-sulfonic acid (FD+C Yellow No. 6); 9-(o-carboxyphenyl)-6-hydroxy-2,4,5,7-tetraiodo-3H-xanthen-3-one monohydrate (FD+C Red No. 3); and 2-(1,3-dihydro-3-oxo-5-sulfo-2H-indol-2-ylidene)-2,3-dihydro-3-oxo-1H-indole-5-sulfonic acid (FD+C Blue No. 2), wherein the suitable colorant should not destabilize the monomer.

The exemplary compositions containing methylene beta-ketoester monomer may also optionally include at least one thickening agent. Suitable thickeners include, for example, polycyanoacrylates, polylactic acid, poly-1,4-dioxa-2-one, polyoxalates, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene. Examples of alkyl methacrylates and acrylates are poly(2-ethylhexyl methacrylate) and poly(2-ethylhexyl acrylate), also poly(butylmethacrylate) and poly(butylacrylate), also copolymers of various acrylate and methacrylate monomers, such as poly(butylmethacrylate-co-methylacrylate).

To improve the cohesive strength of adhesives formed from the compositions containing methylene beta-ketoester monomer, difunctional monomeric cross-linking agents may be added to the monomer compositions of this invention. Such crosslinking agents are known. U.S. Pat. No. 3,940,362 to Overhults, which is hereby incorporated in its entirety by reference, discloses such crosslinking agents.

Other compositions and additives contemplated herein, include additional stabilizers, accelerators, plasticizers, fillers, opacifiers, inhibitors, thixotrophy conferring agents, dyes, fluorescence markers, thermal degradation reducers, adhesion promoters, thermal resistance conferring agents and combinations thereof, and the like, some of which are exemplified by U.S. Pat. Nos. 5,624,669; 5,582,834; 5,575,997; 5,514,371; 5,514,372; 5,312,864 and 5,259,835, the disclosures of all of which are hereby incorporated in their entirety by reference.

Depending on whether the composition is a monomer-based composition (e.g., inks, adhesives, coatings, sealants or reactive molding) or a polymer-based composition (e.g., fibers, films, sheets, medical polymers, composite polymers and surfactants), one having ordinary skill in the art will have the knowledge and skill by which to formulate such compositions and/or products without undue experimentation having suitable amounts, levels and combinations of the above types of additives and components.

Additionally, polymerizable compositions may be formulated to include additives such as acidic stabilizers, a free radical stabilizers, a sequestering agents, a cure accelerators, rheology modifiers, a plasticizing agents, a thixotropic agents, natural rubbers, synthetic rubbers, filler agents, reinforcing agents and the like. Such additives are provided at levels sufficient to achieve the desired results which can readily be determined by those having skill in the art.

For certain exemplary embodiments, an acidic stabilizer is present in a concentration of about 0.1 ppm to about 100 ppm, about 0.1 ppm to about 25 ppm, or about 0.1 ppm to about 15 ppm, by weight of the composition.

For certain exemplary embodiments, a free radical stabilizer is present in a concentration selected from about 0.1 ppm to about 10000 ppm, about 0.1 ppm to about 3000 ppm, about 0.1 ppm to 1500 ppm, about 0.1 ppm to about 1000 ppm, about 0.1 ppm to about 300 ppm, or about 0.1 ppm to about 150 ppm, by weight of the composition.

For certain exemplary embodiments, a sequestering agent, such as a crown ether, a silyl crown, a calixarene, a polyethylene glycol, or a combination thereof may be utilized.

For certain exemplary embodiments, a cure accelerator, such as sodium acetate, potassium acetate, tetrabutyl ammonium fluoride, tetrabutyl ammonium chloride, tetrabutyl ammonium hydroxide, a benzoate salt, a 2,4-pentanedionate salt, a sorbate salt, and a propionate salt, may be utilized.

For certain exemplary embodiments, a rheology modifier, such as hydroxyethylcellulose, ethyl hydroxyethylcellulose, methylcellulose, a polymeric thickener, and pyrogenic silica, may be utilized.

Exemplary polymerizable compositions are stable at 25° C. and at atmospheric pressure for more than 10 days, more than 15 days, more than 20 days, more than 25 days, or more than 30 days. Certain exemplary embodiments may exhibit a shelf life of up to one year, or up to two years. Certain exemplary embodiments may be tested for stability at elevated temperature, e.g., 82° C., at atmospheric pressure. Certain exemplary embodiments may exhibit elevated temperature stability for more than 2 hours.

Certain exemplary embodiments disclosed herein relate to polymers and polymer products formed by polymerization of the polymerizable compositions comprising the methylene beta-ketoester monomers.

Polymers and polymer products envisioned include coatings, paints, fibers, composites, textile fibers, water-treatment polymers, ink carriers, paint carriers, packaging films, moldings, medical polymers, polymer films, polymer fibers, polymer sheets, and the like. As discussed earlier, the methylene beta-ketoester monomers are capable of supporting a vast array of products due to the activity of the methylene group and the ability to vary the functional groups R, R' as shown in the structure of the repeating unit:

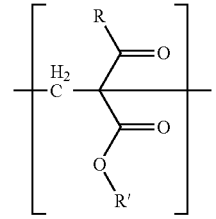

wherein R and R' are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-(C1-C15 alkyl), heteroaryl or heteroaryl-($C_1$-$C_{15}$ alkyl), or alkoxy-(C1-15 alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester.

Oligomeric Complex Products

The reaction of the precursor beta-ketoester with the source of formaldehyde may result in an oligomeric complex which is subsequently cracked to obtain the desired methylene beta-ketoester monomer. Certain oligomeric complexes are capable of being efficiently vaporized or "cracked" into high purity monomers of 2-methylene-1,3-disubstituted-propane-1,3-dione by rapid vaporization as described herein.

As such, the invention provides an oligomeric complex prepared by reacting a 1,3-disubstituted-propane-1,3-dione with a source of formaldehyde; optionally in the presence of heat transfer agent; optionally in the presence of an acidic or basic catalyst; and optionally in the presence of an acidic or non-acidic solvent. In certain embodiments, the oligomeric complex comprises between 2 and 12 repeat units that are able to yield monomer upon cracking The invention further provides an oligomeric complex prepared by reacting a 1,3-disubstituted-propane-1,3-dione with a source of formaldehyde in a substantial absence of acidic solvent; optionally in the presence of heat transfer agent; optionally in the presence of an acidic or basic catalyst; and optionally in the presence of a non-acidic solvent. In certain embodiments, the substantial absence of acidic solvent represents less than 1.0%, less than 0.5%, less than 0.2% or less than 0.1% by weight acidic solvent as compared to the total composition of the reaction mixture.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Analytical Methods

The structures of monomers of this invention were confirmed using one or more of the following procedures.

NMR

Samples were diluted in deuterated chloroform prior to 1H NMR spectroscopy at 300 MHz (Bruker). A more concentrated sample was also prepared in a solution of 0.01 M Cr(III) acetoacetonate in deuterated chloroform and was analyzed by quantitative 13C NMR spectroscopy at 75 MHz. Samples were not purified.

Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:
atm atmosphere
br s broad singlet
C Celsius
d doublet
dd doublet of doublets
MM substituted 3-methylene-2,4-pentanebeta-ketoester
HQ hydroquinone
GC-MS Gas Chromatography-Mass Spectroscopy
g gram
h hour, hours
$^1$H NMR proton nuclear magnetic resonance
J coupling constant (NMR spectroscopy)
L liter
M mol·L$^{-1}$ (molar)
m multiplet
MHz megahertz
min minute, minutes
mL milliliter
mM millimolar
mol mole
MS mass spectrum, mass spectroscopy
m/z mass-to-charge ratio
N equivalents·L$^{-1}$ (normal)
NMR Nuclear Magnetic Resonance
pH negative logarithm of hydrogen ion concentration
q quartet
rt room temperature
s singlet
t triplet
RB, RBF round bottom flask The following concrete examples were made in accordance with the reaction scheme set forth above.

Example 1. Reaction of ethyl 4,4-dimethyl-3-oxopentanoate and formaldehyde

A 250 mL round bottom flask was equipped with a heating mantle, an overhead stirrer equipped with a teflon paddle, a thermocouple and an outlet adapter with attached rubber tubing vented to the back of the hood. The round bottom flask was placed on a heating mantle. A 50 g sample of ethyl pivaloylacetate (i.e., 4,4-dimethyl-3-oxopentanoate), 4.8 g of paraformaldehyde and 0.06 g of zinc acetate were added to the round bottom flask to form a heterogeneous mixture. After 2 minutes of mixing the temperature was set to 100° C. and heating was started. After 5 minutes of reaction time at a temperature of 55° C., the mixture began to clarify. After an additional 30 seconds an exotherm was observed at an approximate temperature of 65.5° C. At this point heating was stopped and the reaction was allowed to proceed. A maximum temperature of 122.1° C. was attained after 8 minutes. The crude product was allowed to cool to room temperature at which time a viscous light yellow liquid was obtained. An aliquot of this material was analyzed by 1H and 13C NMR. This oligomeric material was then depolymerized/cracked as detailed below.

A 4-neck 250 mL round bottom flask was fitted with a mechanical stirrer, an addition funnel, a thermocouple attached to a temperature controller, a Claisen distillation head, vacuum adapter connected to a one-neck 100 mL round bottom flask placed in an ice bath. The system was evacuated to 100 mmHg after which heat was then applied via a heating mantle. When the set temperature reached 190° C., the oligomer was slowly added to the hot cracking flask. The resulting crude monomer was simultaneously cracked and distilled to the receiving flask. During the distillation phase an average head temperature of 155° C. was observed. After the addition was completed, the heat source was turned off and the system was allowed to cool to room temperature. The crude pale green monomer was then analyzed by $^1$H and $^{13}$C NMR.

The following monomer was obtained.

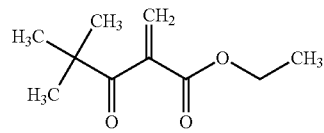

Figure 2:
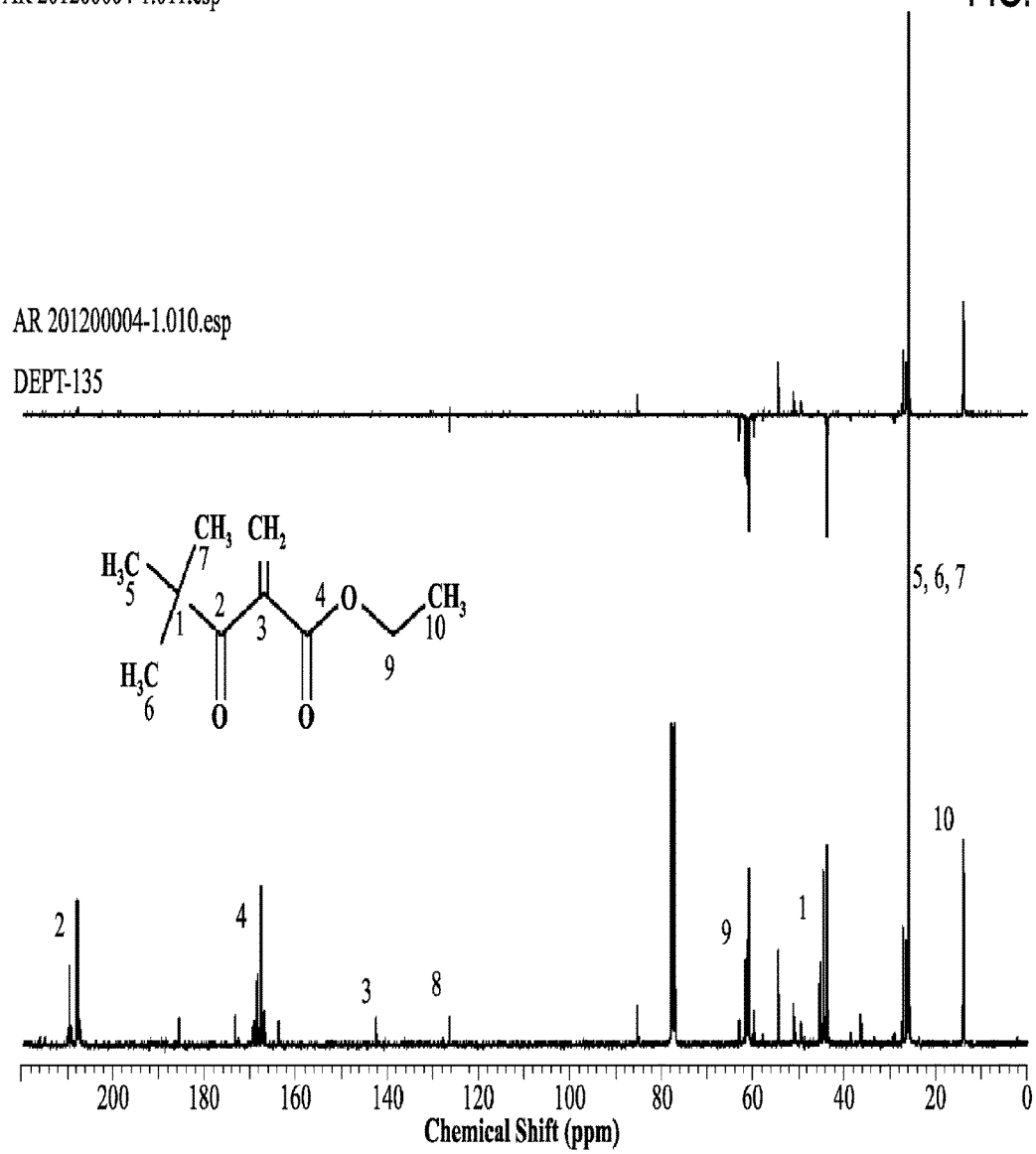

FIGS. 1 and 2 show the $^1$H, $^{13}$C, and DEPT-135 NMR spectra of the isolation step ("crack") in this reaction. Peaks at 5.6 and 6.3 ppm in the $^1$H and 126 ppm in the $^{13}$C NMR spectrum correspond to the geminal CH$_2$ species and the quaternary peak at 142 ppm are consistent with the product.

Example 2. Reaction of ethyl 3-oxo-3-phenylpropanoate with formaldehyde

The reaction scheme disclosed herein was performed using ethyl 3-oxo-3-phenylpropanoate and formaldehyde (obtained from paraformaldehyde). The following monomer was obtained.

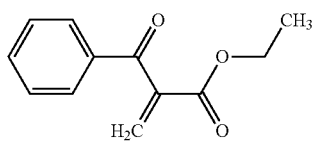

Figure 3:
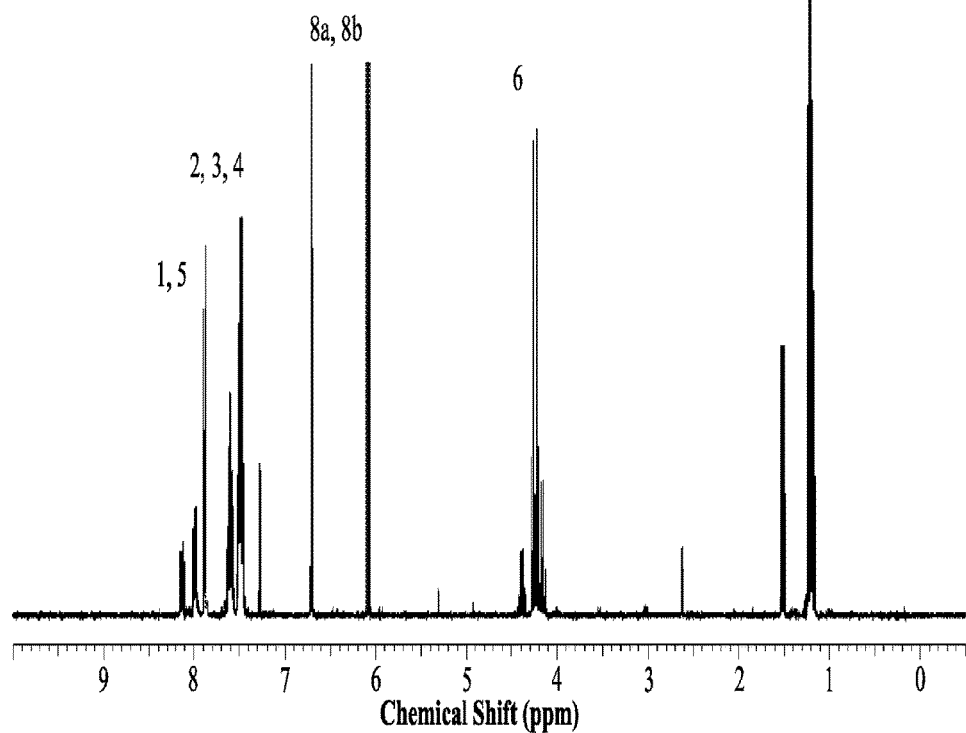
FIGS. 3 and 4 depict NMR spectra demonstrating evidence of a methylene beta-ketoester reaction product formed by the reaction of ethyl 3-oxo-3-phenylpropanoate with formaldehyde.
Figure 4:
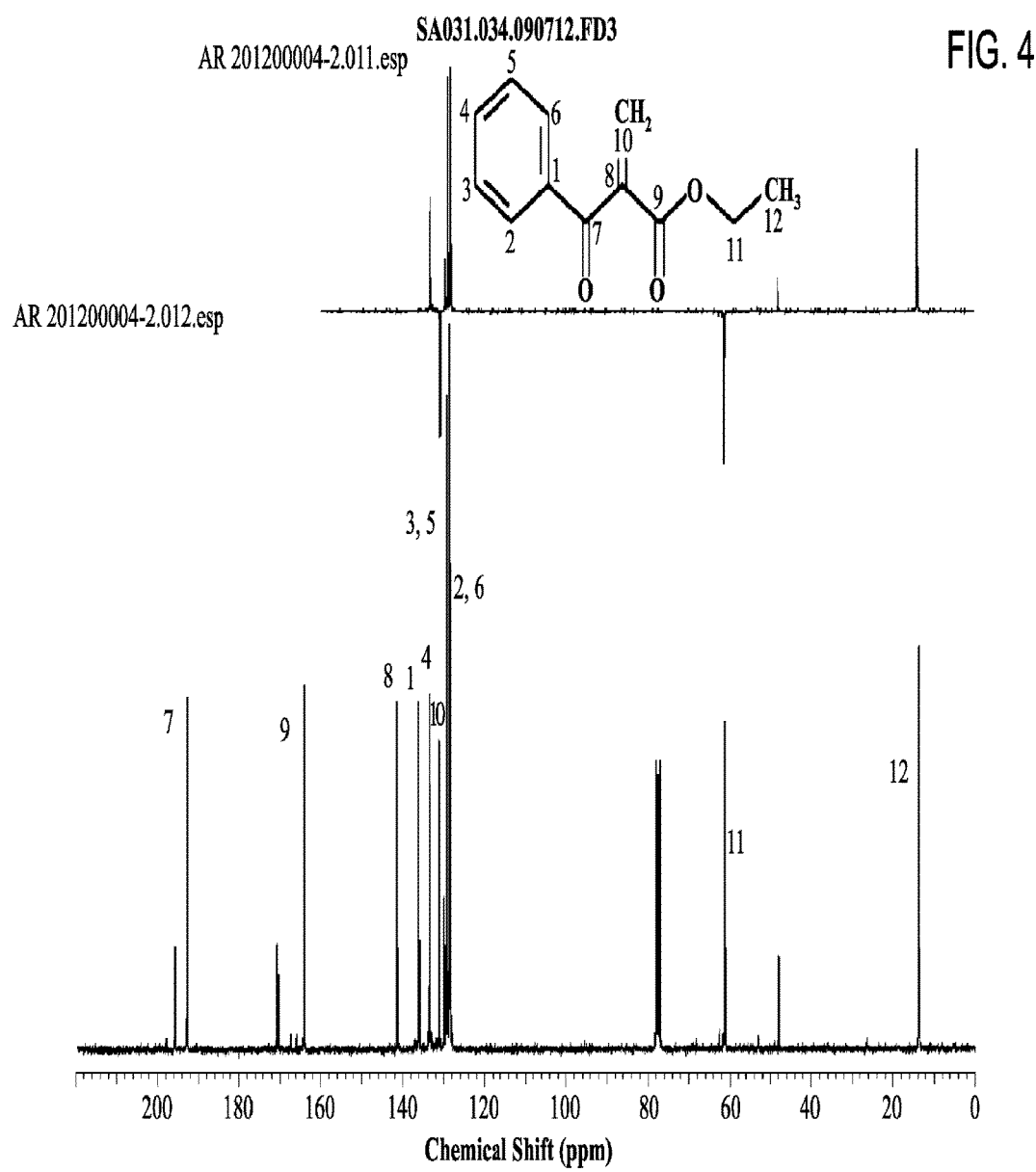

FIGS. 3 and 4 show peaks at 6.1 and 6.7 ppm in the $^1$H NMR spectrum and a peak at 131 ppm in the $^{13}$C NMR spectrum corresponding to the geminal CH$_2$ peak and a quaternary peak at 142 ppm, which are consistent with the product.

Example 3. Reaction of ethyl 3-oxohexanoate with formaldehyde

The reaction scheme disclosed herein was performed using ethyl 3-oxohexanoate and formaldehyde (obtained from paraformaldehyde). The following monomer was obtained.

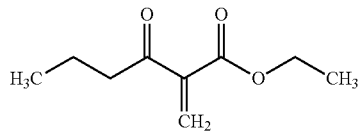

Figure 5:
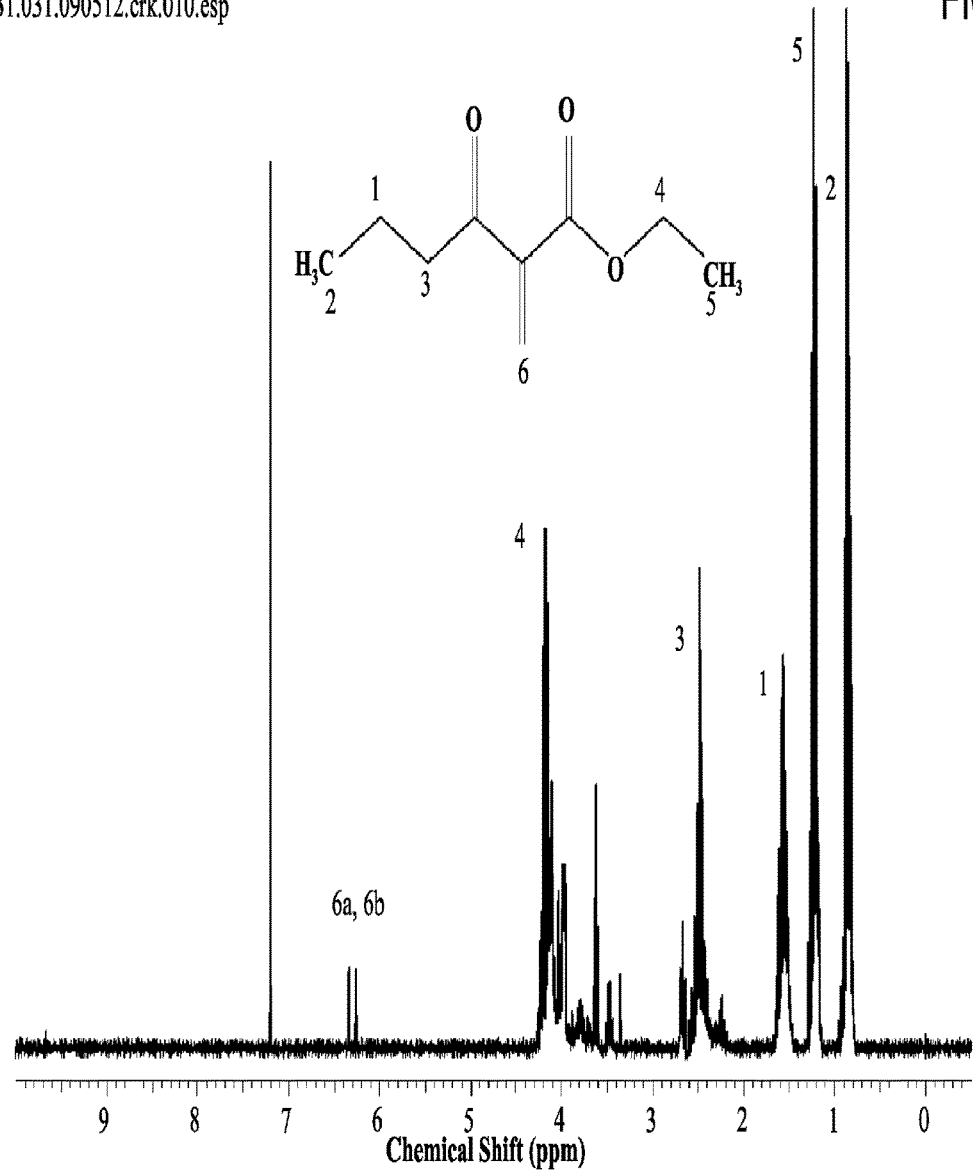
FIG. 5 depicts an NMR spectrum demonstrating evidence of a methylene beta-ketoester reaction product formed by the reaction of ethyl 3-oxo-hexanoate with formaldehyde.

FIG. 5 shows the $^1$H NMR spectrum. Peaks at 6.25 and 6.35 ppm are consistent with the geminal CH$_2$ of the product.

Example 4. Reaction of ethyl 3-oxobutanoate with formaldehyde

The reaction scheme disclosed herein was performed using ethyl 3-oxobutanoate and formaldehyde (obtained from paraformaldehyde). The following monomer was obtained.

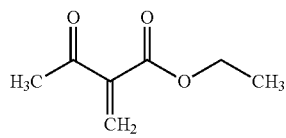

Figure 6:
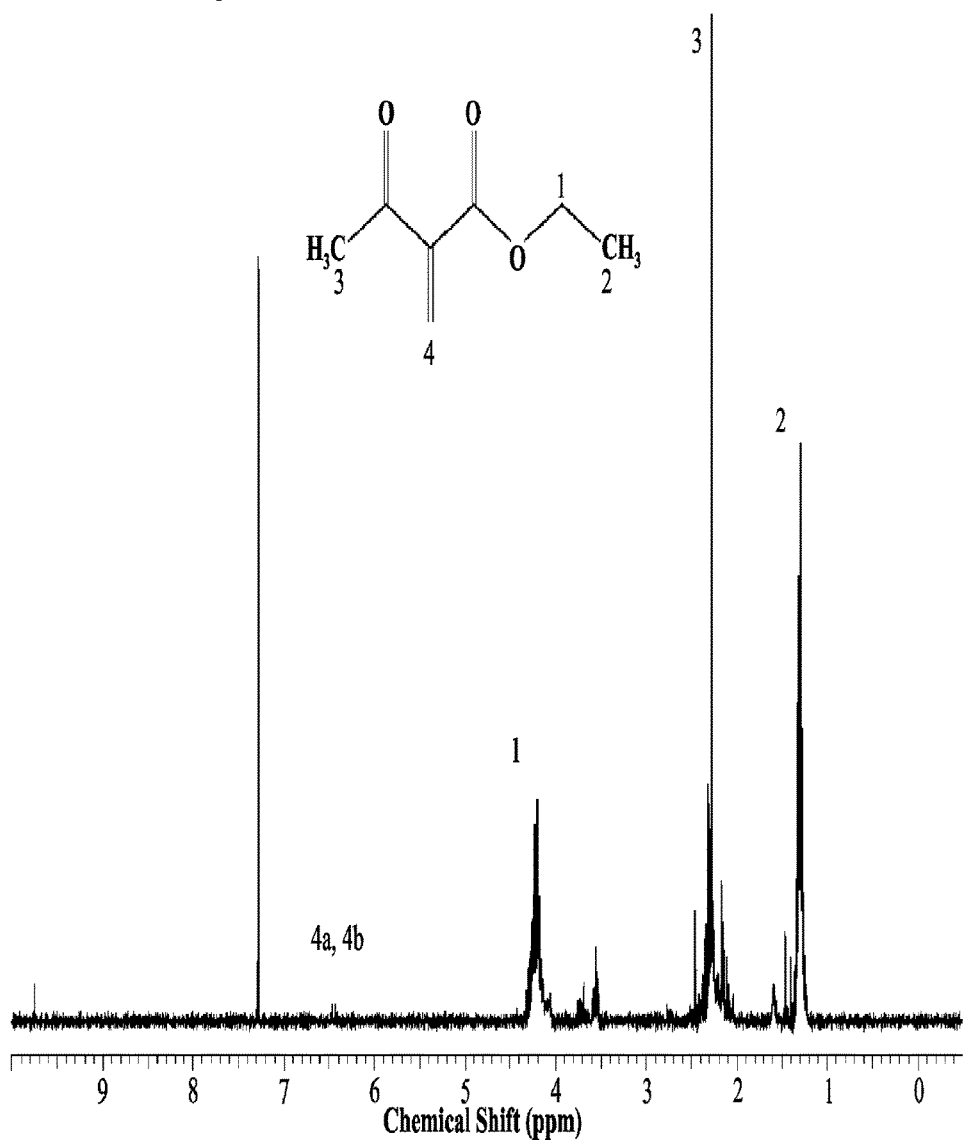
FIG. 6 depicts an NMR spectrum demonstrating evidence of a methylene beta-ketoester reaction product formed by the reaction of ethyl 3-oxobutanoate with formaldehyde.

FIG. 6 shows the $^1$H NMR spectrum. The two small peaks at 6.4 and 6.5 ppm are consistent with the geminal CH$_2$ of the product.

Example 5. Reaction of methyl 3-oxobuanoate with formaldehyde

The reaction scheme disclosed herein was performed using methyl 3-oxobuanoate and formaldehyde (obtained from paraformaldehyde). The following monomer was obtained.

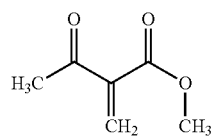

Figure 7:
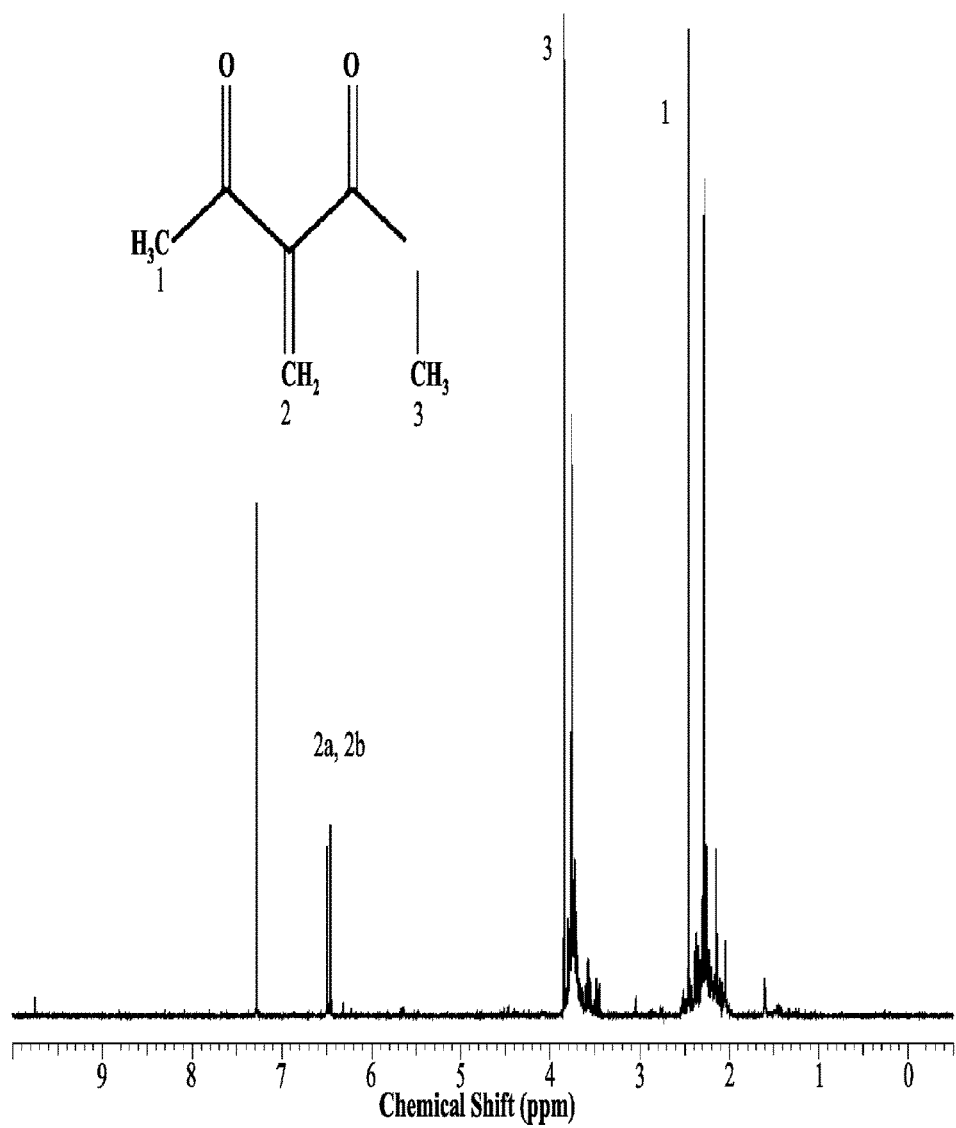
FIG. 7 depicts an NMR spectrum demonstrating evidence of a methylene beta-ketoester reaction product formed by the reaction of methyl 3-oxobuanoate with formaldehyde.

FIG. 7 shows the $^1$H NMR spectrum. The peaks at 6.4 and 6.5 ppm are consistent with the geminal CH$_2$ of the product Example 6. Reaction of ethyl 4-methyl-3-oxopentanoate with formaldehyde The reaction scheme disclosed herein was performed using ethyl 4-methyl-3-oxopentanoate and formaldehyde (obtained from paraformaldehyde). The following monomer was obtained.

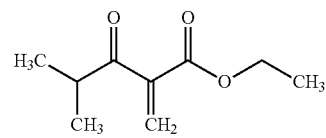

Figure 8:
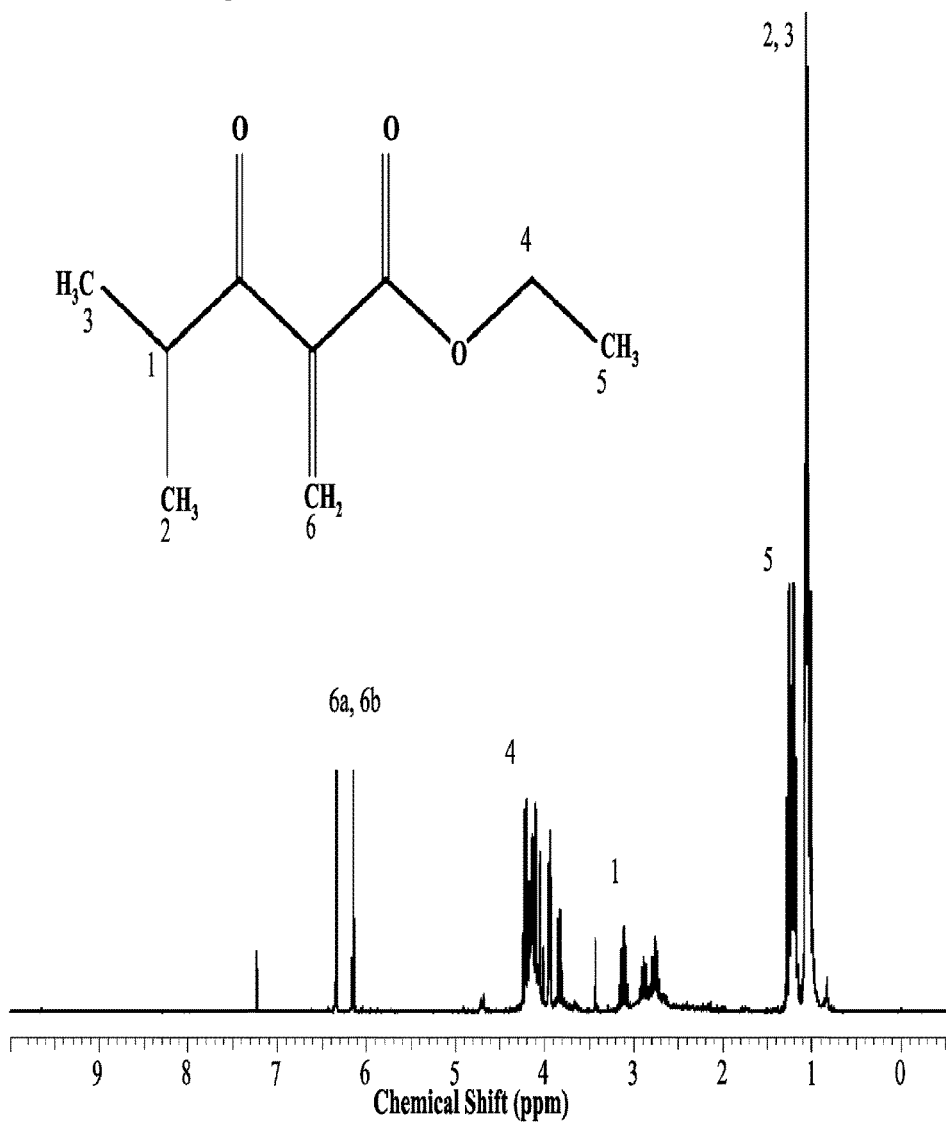
FIG. 8 depicts an NMR spectrum demonstrating evidence of a methylene beta-ketoester reaction product formed by the reaction of ethyl 4-methyl-3-oxopentanoate with formaldehyde.

FIG. 8 shows the $^1$H NMR spectrum. The peaks at 6.15 and 6.35 ppm are consistent with the geminal CH$_2$ of the product.

Example 7. Reaction of ethyl 3-oxopenanoate with formaldehyde

The reaction scheme disclosed herein was performed using ethyl 3-oxopenanoate and formaldehyde (obtained from paraformaldehyde). The following monomer was obtained.

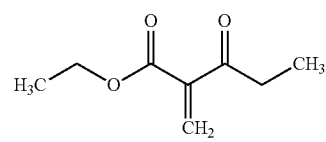

Figure 9:
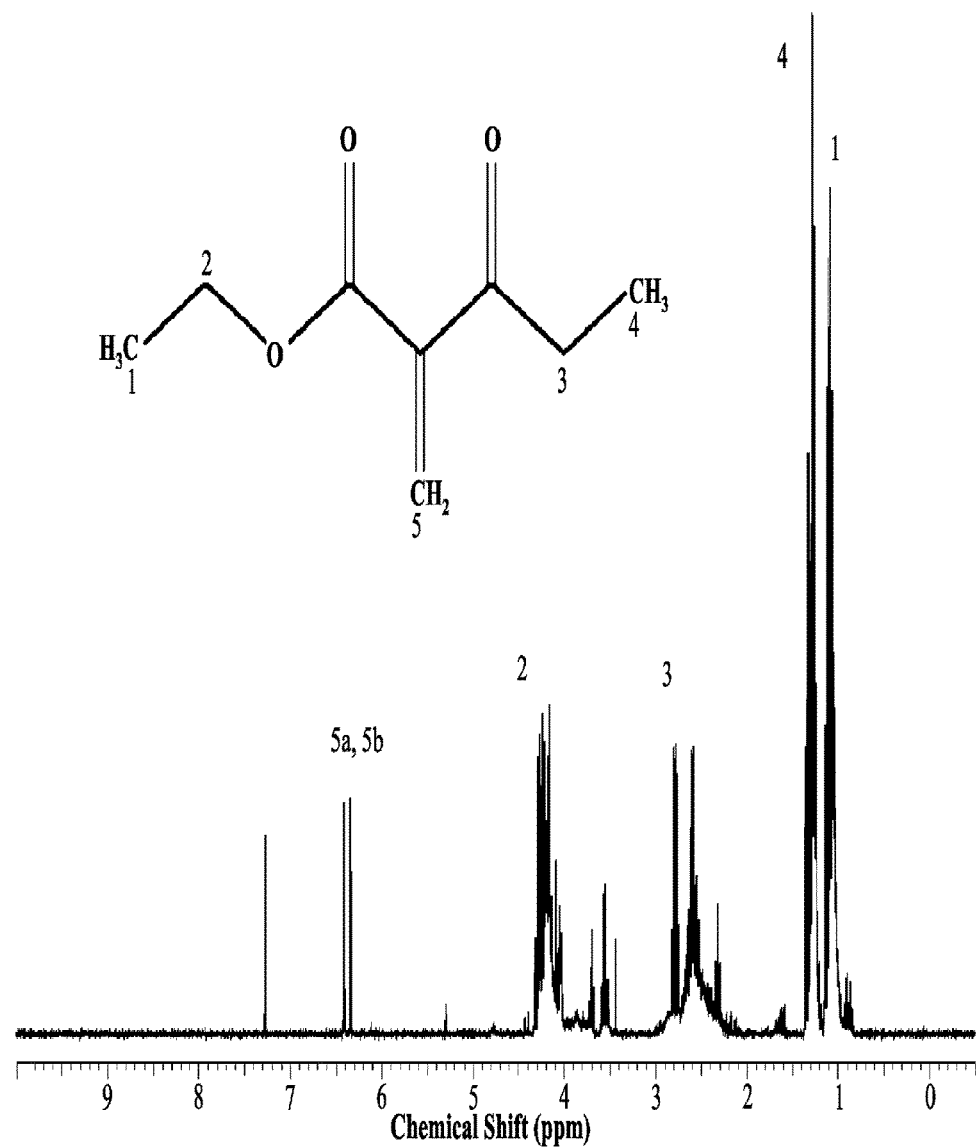
FIG. 9 depicts an NMR spectrum demonstrating evidence of a methylene beta-ketoester reaction product formed by the reaction of ethyl 3-oxopenanoate with formaldehyde.

FIG. 9 shows the $^1$H NMR spectrum. The peaks at 6.3 and 6.4 ppm are consistent with the geminal CH$_2$ of the product.

Example 8. Additional Examples

The reaction scheme disclosed herein is performed using an appropriate beta-ketoester reactant and a source of formaldehyde to obtain the following monomers.

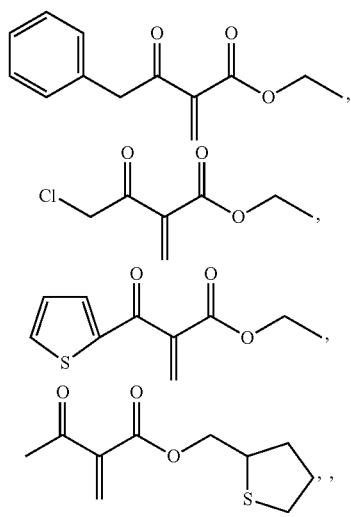

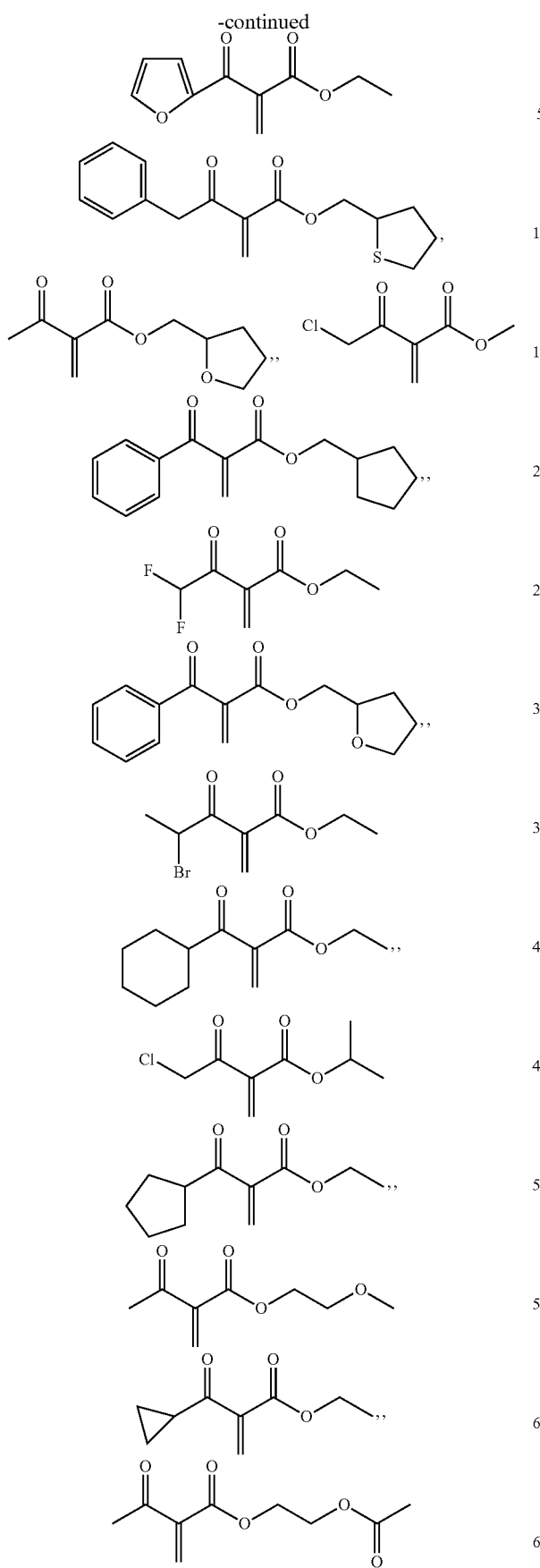

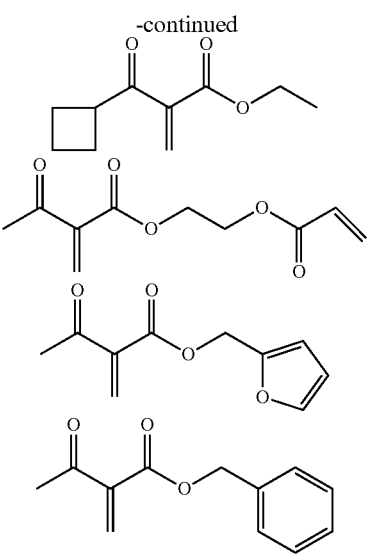

Equivalents

Those skilled in the art will recognize, or be able to ascertain using no more than routine experimentation, many equivalents to the specific embodiments of the invention described herein. Such equivalents are intended to be encompassed by this invention.

What is claimed is:

1. A polymer prepared from a polymerizable composition comprising:
    at least one methylene beta-ketoester monomer having the structural formula:

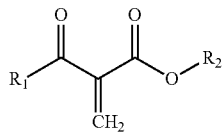

wherein $R_1$ and $R_2$ are independently $C_1$-$C_{15}$ alkyl, $C_2$-$C_{15}$ alkenyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl-($C_1$-$C_{15}$ alkyl), heteroaryl or heteroaryl-($C_1$-$C_{15}$ alkyl), each of which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl □($C_1$-$C_{15}$ alkyl), heteroaryl, $C_1$-$C_{15}$ alkylthio, hydroxyl, nitro, azido, cyano, acyloxy, carboxy, or ester;

or wherein $R_1$ and $R_2$ are taken together with the atoms to which they are bound to form a 5-7membered heterocyclic ring which may be optionally substituted by $C_1$-$C_{15}$ alkyl, halo-($C_1$-$C_{15}$ alkyl), $C_3$-$C_6$ cycloalkyl, halo-($C_3$-$C_6$ cycloalkyl), heterocyclyl, heterocyclyl-($C_1$-$C_{15}$ alkyl), aryl, aryl □($C_1$-$C_{15}$ alkyl), heteroaryl, $C_1$-$C_{15}$ alkoxy, $C_1$-$C_{15}$ alkylthio, hydroxyl, nitro, azido, cyano, acyloxy, carboxy, or ester; and wherein the amount of ketals in the polymerizable composition is less than about 100 ppm and/or the amount of latent acid-forming impurities in the polymerizable composition is less than about 100 ppm.

2. The polymer prepared from the polymerizable composition of claim 1, wherein the polymer includes a difunctional monomeric cross-linking agent.

3. The polymer prepared from the polymerizable composition of claim 1, wherein $R_1$ and $R_2$ are independently $C_1$-$C_6$ alkyl or aryl.

4. The polymer prepared from the polymerizable composition of claim 1, wherein the methylene beta-ketoester monomer has the structure:

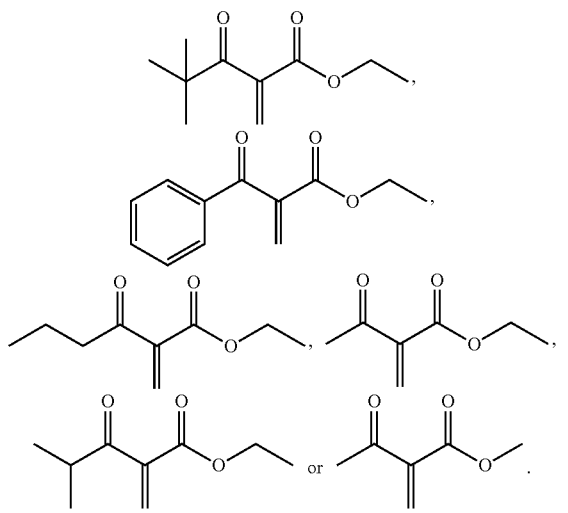

5. The polymer prepared from the polymerizable composition of claim 1, wherein the methylene beta-ketoester monomer has the structure:

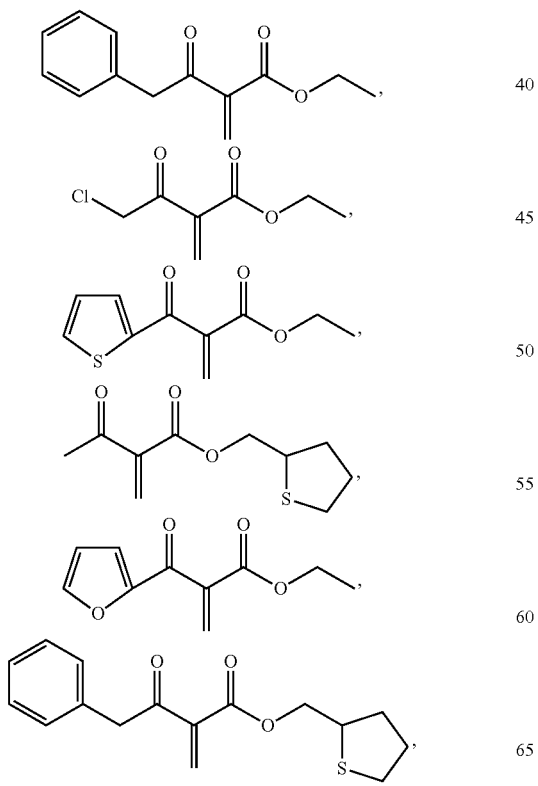

-continued

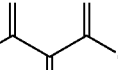

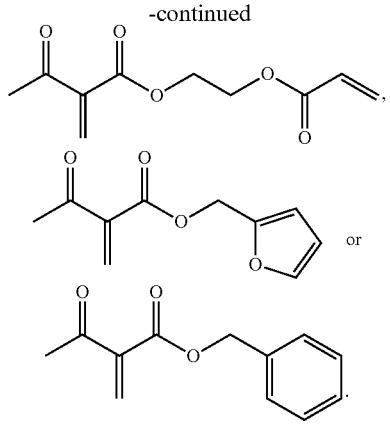

6. The polymer prepared from the polymerizable composition of claim 1 further comprising one or more components which include tougheners, plasticizers, thixotropic agents, rubbers or reinforcing agents.

7. The polymer prepared from the polymerizable composition of claim 1, wherein the polymer is a fiber, a film, a sheet, a medical polymer, a composite polymer or a surfactant.

* * * * *